US006875568B2

(12) United States Patent
Nisson et al.

(10) Patent No.: US 6,875,568 B2
(45) **Date of Patent: *Apr. 5, 2005**

(54) METHOD FOR ISOLATING AND RECOVERING TARGET DNA OR RNA MOLECULES HAVING A DESIRED NUCLEOTIDE SEQUENCE

(75) Inventors: Paul E. Nisson, Gaithersburg, MD (US); Joel Jesse, Mt. Airy, MD (US); Wu-bo Li, N. Potomac, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/829,066

(22) Filed: Apr. 10, 2001

(65) Prior Publication Data

US 2002/0076708 A1 Jun. 20, 2002

Related U.S. Application Data

(63) Continuation of application No. 09/103,577, filed on Jun. 24, 1998, now Pat. No. 6,268,133.

(60) Provisional application No. 60/050,729, filed on Jun. 25, 1997.

(51) Int. Cl.[7] .......................... C12Q 1/68; C12P 19/34; C07H 21/02; C07H 21/04; C07H 21/00

(52) U.S. Cl. ......................... 435/6; 435/91.1; 536/23.1; 536/24.3; 536/24.33; 536/25.3

(58) Field of Search .......................... 435/6, 71.1, 183; 436/94; 536/23.1, 24.3; 530/300, 350

(56) References Cited

U.S. PATENT DOCUMENTS

| | | | | |
|---|---|---|---|---|
| 4,683,202 A | | 7/1987 | Mullis | 435/91 |
| 4,767,699 A | | 8/1988 | Vary et al. | 435/6 |
| 4,800,159 A | | 1/1989 | Mullis et al. | 435/172.3 |
| 5,165,925 A | | 11/1992 | Leong | 424/88 |
| 5,187,085 A | | 2/1993 | Lee | 435/91 |
| 5,350,672 A | | 9/1994 | Oberst et al. | 435/6 |
| 5,484,702 A | | 1/1996 | Ludwig | 435/6 |
| 5,500,356 A | | 3/1996 | Li et al. | 435/91.1 |
| 5,545,540 A | | 8/1996 | Mian | 435/91.2 |
| 5,650,167 A | * | 7/1997 | Allison | 424/451 |
| 5,719,023 A | * | 2/1998 | Zarling et al. | 435/6 |
| 5,759,778 A | | 6/1998 | Li et al. | 435/6 |
| 5,871,929 A | | 2/1999 | Barnes | 435/6 |
| 6,013,488 A | | 1/2000 | Hayashizaki | 435/91.51 |
| 6,268,133 B1 | * | 7/2001 | Nisson et al. | 435/6 |

FOREIGN PATENT DOCUMENTS

| | | |
|---|---|---|
| DE | 44 11 588 C1 | 9/1995 |
| DE | 44 11 594 C1 | 12/1995 |
| EP | 773 225 A3 | 5/1997 |
| EP | 0 773 225 A2 | 5/1997 |
| EP | 0 821 059 A2 | 1/1998 |
| FR | 2 733 515 A1 | 10/1996 |
| WO | WO 95/09915 | 4/1995 |
| WO | WO 95/20682 | 8/1995 |
| WO | WO 97/20918 | 6/1997 |

OTHER PUBLICATIONS

Mitchell et al., Affinity generation of single–stranded DNA for dideoxy sequencing following the polymerase chain reaction. Anal. Biochem., 178, 239–242, 1989.*

Inman et al., Partial denaturation of thymine– and 5–bromouracil–containing lambda DNA in alkali. J. Mol. Biol., 49, 93–98, 1970.*

Liquier et al., Infrared linear dichroism investigations of deoxyribonucleic acid complexes with poly(l–arginine) and poly(–lysine). Biochemistry, 14, 4191–4197, 1975.*

Freifelder, Physical Biochemistry: Applications to Biochemistry and Molecular Biology, second edition, pp. 508–510, 1982. Published by W.h. Freeman and company, San Francisco.*

Yoshida, Mg2+, Ca2+–dependent unwinding of DNA by poly–L–glutamic acid. Biochem. Biophys. Res. Commun., 116, 217–221, 1983.*

Smol'yaninova, T.I., et al., "Model Studies of DNA–Protein Interactions. I. Effect of Aminocarboxylic and Amide Groups of Amino Acids on the Thermostability and Conformation of DNA," *Molekulyarnaya Biologiya* 19:992–1000, Maik Nauka/Interperiodica Publishing (1985).

Aslanyan, V.M. et al., "Conformation and Thermal Stability of DNA in Aqueous Solutions of β–Alanine and γ–Aminobutyric Acid," *Biophysics* 29:615–620, Pergamon Press Ltd. (1984).

Baskaran, N. et al., "Uniform Amplification of a Mixture of Deoxyribonucleic Acids with Varying GC Content," *Genome Res.* 6:633–638, Cold Spring Harbor Laboratory Press (Jul. 1996).

Buche, A. et al., "Organic Osmotic Effectors and Chromatin Structure," *J. Biomol. Struct. & Dynam.* 8:601–618, Adenine Press (1990).

(Continued)

*Primary Examiner*—Kenneth R. Horlick
*Assistant Examiner*—Frank Lu
(74) *Attorney, Agent, or Firm*—Sterne, Kessler, Goldstein & Fox P.L.L.C.

(57) ABSTRACT

The invention generally concerns the use of amino acid denaturants for denaturing or separating double stranded nucleic acid molecules. More specifically, the present invention provides a method for the rapid isolation and recovery of a desired target DNA or RNA molecules from a mixture or library containing such molecules. The method involves the use of haptenylated probes and amino acid denaturants to select the desired molecules and eliminate the undesired library members from a sample. The invention also provides a method in which larger or full-length nucleic acid molecules can be isolated from the subpopulation of desired molecules.

23 Claims, 3 Drawing Sheets

OTHER PUBLICATIONS

Buche, A. et al., "Glycine and other amino compounds prevent chromatin precipitation at physiological ionic strength," FEBS Lett. 247:367–370, Federation of European Biochemical Societies and Elsevier Science Publishers B.V. (Biomedical Division) (1989).

Buche, A. et al., "Effect of Organic Effectors on Chromatin Solubility, DNA–Histone H1 Interactions, DNA and Histone H1 Structures," *J. Biomol. Struct. & Dynam.* 11:95–119, Adenine Press (1993).

Cánovas, D. et al., "Osmoprotectants in *Halomonas elongata*: High–Affinity Betaine Transport System and Choline–Betaine Pathway," *J. Bacteriol.* 178:7221–7226, American Society for Microbiology (Dec. 1996).

Cánovas, D. et al., "Isolation and Characterization of Salt–sensitive Mutants of the Moderate Halophile *Halomonas elongata* and Cloning of the Ectoine Synthesis Genes," *J. Biol. Chem.* 272:25794–25801, The American Society for Biochemistry and Molecular Biology, Inc. (Oct. 1997).

Carninci, P. et al., "Thermostabilization and thermoactivation of thermolabile enzymes by trehalose and its application for the synthesis of full length cDNA," *Proc. Natl. Acad. Sci. USA* 95:520–524, The National Academy of Sciences (Jan. 1998).

Chambers, S.T. et al., "Dimethylthetin Can Substitute for Glycine Betaine as an Osmoprotectant Molecule for *Escherichia coli*," *J. Bacteriol.* 169:4845–4847, American Society for Microbiology (1987).

Flock, S. et al., "Osmotic Effectors and DNA Structure: Effect of Glycine on Precipitation of DNA by Multivalent Cations." *J. Biomol. Struct. & Dynam.* 13:87–102, Adenine Press (1995).

Flock, S. et al., "Dielectric Constant and Ionic Strength Effects on DNA Precipitation," *Biophys. J.* 70:1456–1465, Biophysical Society (Mar. 1996).

Flock, S. et al., "$^{23}$Na NMR Study of the Effect of Organic Osmolytes on DNA Counterion Atmosphere," *Biophys. J.* 71:1519–1529, Biophysical Society (Sep. 1996).

Frackman, S. et al., "Betaine and DMSO: Enhancing Agents for PCR," *Promega Notes* 65:27–29, Promega Corporation (Feb. 1998).

Gouesbet, G. et al., "Characterization of the *Erwinia chrysanthemi* Osmoprotectant Transporter Gene ousA," *J. Bacteriol.* 178:447–455, American Society for Microbiology (Jan. 1996).

Hengen, P.N., "Optimizing multiplex and LA–PCR with betaine," *Trends Biochem. Sci.* 22:225–226, Elsevier Science Ltd. (Jun. 1997).

Henke, W. et al., "Betaine improves the PCR amplification of GC–rich DNA sequences," *Nucl. Acids Res.* 25:3957–3958, Oxford University Press (Oct. 1997).

Hogrefe, H. et al., "Novel PCR Enhancing Factor Improves Performance of Pfu DNA Polymerase," *Stratagene Strategies* 10:93–96, Stratagene (Aug. 1997).

Houssier, C. et al., "Effects of Compensatory Solutes on DNA and Chromatin Structural Organization in Solution," *Comp. Biochem. Physiol.* 117A:313–318, Elsevier Science Inc. (Jul. 1997).

Iakobashvili, R. and Lapidot, A., "Low temperature cycled PCR protocol for Klenow fragment of DNA polymerase I in the presence of proline," *Nucl. Acids Res.* 27: 1566–1568, Oxford University Press (Mar. 1999).

Jakob, R. and Saenger, W., "Reversed–phase ion–pair chromatographic separation of ribulose 1,5–bisphosphate from 3–phosphoglycerate and its application as a new enzyme assay for RuBP carboxylase/oxygenase," *FEBS Lett.* 183:111–114, Elsevier Science Publishers B.V. (Biomedical Divion) (1985).

Kondakova, N.V. et al., "Effect of Low–molecular Amines on DNA Conformation and Stability of Double Helix," *Molekulyarnaya Biologiya* 9:742–745, Maik Nauka/Interperiodica Publishing (1975).

English Language Translation for Document AS8, Kondakova, N.V. et al., "Effect of Low molecular Amines on the Conformation and Stability of the DNA Double Helix," *Molekulyarnaya Biologiya* 9:742–746, Plenum Publishing Corporation (1975).

Landre, P.A. et al., "The Use of Cosolvents to Enhance Amplification by the Polymerase Chain Reaction," in *PCR Strategies*, Innis, M.A. et al., eds., Academic Press, Inc., San Diego, California, pp. 3–16 (1995).

Le Rudulier, D. et al., "Molecular Biology of Osmoregulation," *Science* 224:1064–1068, American Association for the Advancement of Science (1984).

Li, C.–J. et al., "Nonprotein Amino Acids from Seeds of *Cycas circinalis* and *Phaseolus vulgaris,*" *Phytochem.* 42:443–445, Elsevier Science Ltd. (May 1996).

Malin, G. and Lapidot, A., "Induction of Synthesis of Tetrahydropyrimidine Derivatives in *Streptomyces* Strains and Their Effect on *Escherichia coli* in Response to Osmotic and Heat Stress," *J. Bacteriol.* 178:385–395, American Society for Microbiology (Jan. 1996).

Marquet, R. and Houssier, C., "Thermodynamics of Cation–Induced DNA Condensation," *J. Biomol. Struct. & Dynam.* 9:159–167, Adenine Press (1991).

Mytelka, D.S. and Chamberlin, M.J., "Analysis and suppression of DNA polymerase pauses associated with a trinucleotide consensus," *Nucleic Acids Res.* 24:2774–2781, Oxford University Press (Jul. 1996).

Panaccio, M. et al., "FoLT PCR: A Simple PCR Protocol for Amplifying DNA Directly from Whole Blood," *BioTechniques* 14:238–243, Eaton Publishing Company (1993).

Rafferty, J.A. and Fletcher, H.L., "Sequence Analysis of a Family of Highly Repeated DNA Units in *Stauroderus scalaris* (Orthoptera)," *Int. J. Genome Res.* 1:1–16, World Scientific Publishing Company (1992).

Rajendrakumar, C.S.V. et al., "DNA helix destabilization by proline and betaine: possible role in the salinity tolerance process," *FEBS Lett.* 410:201–205, Federation of European Biochemical Societies (Jun. 1997).

Randall, K. et al., "Accumulation of natural and synthetic betaines by a mammalian renal cell line," *Biochem. Cell Biol.* 74:283–287, National Research Council Canada (Apr. 1996).

Randall, K. et al., "Natural and syntheic betaines counter the effects of high NaC1 and urea concentrations," *Biochim. Biophys. Acta* 1291:189–194, Elsevier Science B.V. (Dec. 1996).

Rees, W.A. et al., "Betaine Can Eliminate the Base Pair Composition Dependence of DNA Melting," *Biochemistry* 32:137–144, American Chemical Society (1993).

Shepard, A.R. and Rae, J.L., "Magnetic bead capture of cDNAs from double–stranded plasmid cDNA libraries," *Nucleic Acids Res.* 25:3183–3185, Oxford University Press (Aug. 1997).

Solomons, T.W.G., "Organic Chemistry, 5th Edition", John Wiley & Sons, Inc., New York, N.Y., p. 1094 (1992).
Urdea, M.S., "Branched DNA Signal Amplification," *Bio/Technology* 12:926, 928, Nature Publishing Company (1994).
Varadaraj, K. and Skinner, D.M., "Denaturants or cosolvents improve the specificity of PCR amplification of a G+C–rich DNA using genetically engineered DNA polymerases," *Gene* 140:1–5, Elsevier Science B.V. (1994).
Weissensteiner, T. and Lanchbury, J.S., "Strategy for Controlling Preferential Amplification and Avoiding False Negatives in PCR Typing," *BioTechniques* 21:1102–1108, Eaton Publishing Co. (Dec. 1996).
Woodford, K. et al., "The use of $K^+$–free buffers eliminates a common cause of premature chain termination in PCR and PCR sequencing," *Nucl. Acids Res.* 23:539, Oxford University Press (1995).
Bioactive Peptides, 1993 Sigma Chemical Company Catalogue, St. Louis, MO, pp. 1028–1034.
Instruction Manual for "GeneTrapperTM cDNA Positive Selection System," Catalog No. 10356–020, GIBCO BRL, Life Technologies, Gaithersburg, MD (Jul. 1996).
Life Technologies product catalogue and reference guide, 1995, p. 19–10 and 19–12.

Dialog File 351, Derwent WPI Accession No. 95–329356/199543, English language abstract for German Patent No. 4411588.

Dialog File 351, Derwent WPI Accession No. 96–021044/199603, English language abstract for German Patent No. 4411594.

Lin, P. K. T. and Brown, D. M., "Synthesis and duplex stability of oligonucleotides containing cytosine–thymine analogues," *Nucleic Acid Research* 17:10373–10383, IRL Press at Oxford University Press (1989).

Lin, P. K. T. and Brown, D. M., "Synthesis of oligodeoxyribonucleotides containing degenerate bases and their use as primers in the polymerase chain reaction," *Nucleic Acid Research* 20:5149–5152, IRL Press at Oxford University Press (1992).

* cited by examiner

FIG.2 OVERVIEW OF GENE II-Exo III DIGESTION AND CAT OLIGONUCLEOTIDE BINDING

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: degenerate oligonucleotide
<221> NAME/KEY: misc_feature
<222> LOCATION: 3
<223> OTHER INFORMATION: where n is g, t, a, or c
<221> NAME/KEY: misc_feature
<222> LOCATION: 12
<223> OTHER INFORMATION: where n is g, t, a, or c
<221> NAME/KEY: misc_feature
<222> LOCATION: 21
<223> OTHER INFORMATION: where n is g, t, a, or c

<400> SEQUENCE: 1
```

-continued gtn tgy gay ggn tty cay gtn gg 23

<210> SEQ ID NO 2
<211> LENGTH: 23
<212> TYPE: DNA
<213> ORGANISM: Artificial Sequence
<220> FEATURE:
<223> OTHER INFORMATION: degenerate oligonucleotide
<221> NAME/KEY: misc_feature
<222> LOCATION: 3
<223> OTHER INFORMATION: where n is 2-amino-6-methoxyaminopurine
<221> NAME/KEY: misc_feature
<222> LOCATION: 6
<223> OTHER INFORMATION: where n is 6H,8H-3,4-dihydropyrimido[4,5-c][1,
2]oxazin-7-one
<221> NAME/KEY: misc_feature
<222> LOCATION: 9
<223> OTHER INFORMATION: where n is 6H,8H-3,4-dihydropyrimido[4,5-c][1,
2]oxazin-7-one<221> NAME/KEY: misc_feature
<222> LOCATION: 12
<223> OTHER INFORMATION: where n is 2-amino-6-methoxyaminopurine
<221> NAME/KEY: misc_feature
<222> LOCATION: 15
<223> OTHER INFORMATION: where n is 6H,8H-3,4-dihydropyrimido[4,5-c][1,
2]oxazin-7-one
<221> NAME/KEY: misc_feature
<222> LOCATION: 18
<223> OTHER INFORMATION: where n is 6H,8H-3,4-dihydropyrimido[4,5-c][1,
2]oxazin-7-one
<221> NAME/KEY: misc_feature
<222> LOCATION: 21
<223> OTHER INFORMATION: where n is 2-amino-6-methoxyaminopurine

<400> SEQUENCE: 2 gtn tgn gan ggn ttn can gtn gg 23

<210> SEQ ID NO 3
<211> LENGTH: 23
<212> TYPE: DNA
<213> ORGANISM: Artificial Sequence
<220> FEATURE:
<223> OTHER INFORMATION: degenerate oligonucleotide
<221> NAME/KEY: misc_feature
<222> LOCATION: 3
<223> OTHER INFORMATION: where n is 2-amino-6-methoxyaminopurine
<221> NAME/KEY: misc_feature
<222> LOCATION: 6
<223> OTHER INFORMATION: where n is 6H,8H-3,4-dihydropyrimido[4,5-c][1,
2]oxazin-7-one
<221> NAME/KEY: misc_feature
<222> LOCATION: 9
<223> OTHER INFORMATION: where n is 6H,8H-3,4-dihydropyrimido[4,5-c][1,
2]oxazin-7-one
<221> NAME/KEY: misc_feature
<222> LOCATION: 12
<223> OTHER INFORMATION: where n is 2-amino-6-methoxyaminopurine
<221> NAME/KEY: misc_feature
<222> LOCATION: 15
<223> OTHER INFORMATION: where n is 6H,8H-3,4-dihydropyrimido[4,5-c][1,
2]oxazin-7-one
<221> NAME/KEY: misc_feature
<222> LOCATION: 18
<223> OTHER INFORMATION: where n is 6H,8H-3,4-dihydropyrimido[4,5-c][1,
2]oxazin-7-one
<221> NAME/KEY: misc_feature
<222> LOCATION: 21
<223> OTHER INFORMATION: where n is 6H,8H-3,4-dihydropyrimido[4,5-c][1,
2]oxazin-7-one

<400> SEQUENCE: 3 gtn tgn gan ggn ttn can gtn gg 23

<210> SEQ ID NO 4

-continued

<211> LENGTH: 23
<212> TYPE: DNA
<213> ORGANISM: Artificial Sequence
<220> FEATURE:
<223> OTHER INFORMATION: degenerate oligonucleotide
<221> NAME/KEY: misc_feature
<222> LOCATION: 3
<223> OTHER INFORMATION: where n is 2-amino-6-methoxyaminopurine
<221> NAME/KEY: misc_feature
<222> LOCATION: 6
<223> OTHER INFORMATION: where n is 6H,8H-3,4-dihydropyrimido[4,5-c][1,2]oxazin-7-one
<221> NAME/KEY: misc_feature
<222> LOCATION: 9
<223> OTHER INFORMATION: where n is 6H,8H-3,4-dihydropyrimido[4,5-c][1,2]oxazin-7-one
<221> NAME/KEY: misc_feature
<222> LOCATION: 12
<223> OTHER INFORMATION: where n is 6H,8H-3,4-dihydropyrimido[4,5-c][1,2]oxazin-7-one
<221> NAME/KEY: misc_feature
<222> LOCATION: 15
<223> OTHER INFORMATION: where n is 6H,8H-3,4-dihydropyrimido[4,5-c][1,2]oxazin-7-one
<221> NAME/KEY: misc_feature
<222> LOCATION: 18
<223> OTHER INFORMATION: where n is 6H,8H-3,4-dihydropyrimido[4,5-c][1,2]oxazin-7-one
<221> NAME/KEY: misc_feature
<222> LOCATION: 21
<223> OTHER INFORMATION: where n is 2-amino-6-methoxyaminopurine

<400> SEQUENCE: 4 gtn tgn gan ggn ttn can gtn gg 23

<210> SEQ ID NO 5
<211> LENGTH: 23
<212> TYPE: DNA
<213> ORGANISM: Artificial Sequence
<220> FEATURE:
<223> OTHER INFORMATION: degenerate oligonucleotide
<221> NAME/KEY: misc_feature
<222> LOCATION: 3
<223> OTHER INFORMATION: where n is 6H,8H-3,4-dihydropyrimido[4,5-c][1,2]oxazin-7-one
<221> NAME/KEY: misc_feature
<222> LOCATION: 6
<223> OTHER INFORMATION: where n is 6H,8H-3,4-dihydropyrimido[4,5-c][1,2]oxazin-7-one
<221> NAME/KEY: misc_feature
<222> LOCATION: 9
<223> OTHER INFORMATION: where n is 6H,8H-3,4-dihydropyrimido[4,5-c][1,2]oxazin-7-one
<221> NAME/KEY: misc_feature
<222> LOCATION: 12
<223> OTHER INFORMATION: where n is 2-amino-6-methoxyaminopurine
<221> NAME/KEY: misc_feature
<222> LOCATION: 15
<223> OTHER INFORMATION: where n is 6H,8H-3,4-dihydropyrimido[4,5-c][1,2]oxazin-7-one
<221> NAME/KEY: misc_feature
<222> LOCATION: 18
<223> OTHER INFORMATION: where n is 6H,8H-3,4-dihydropyrimido[4,5-c][1,2]oxazin-7-one
<221> NAME/KEY: misc_feature
<222> LOCATION: 21
<223> OTHER INFORMATION: where n is 2-amino-6-methoxyaminopurine

<400> SEQUENCE: 5 gtn tgn gan ggn ttn can gtn gg 23

<210> SEQ ID NO 6
<211> LENGTH: 23
<212> TYPE: DNA
<213> ORGANISM: Artificial Sequence -continued
<220> FEATURE:
<223> OTHER INFORMATION: degenerate oligonucleotide
<221> NAME/KEY: misc_feature
<222> LOCATION: 3
<223> OTHER INFORMATION: where n is 6H,8H-3,4-dihydropyrimido[4,5-c][1,
2]oxazin-7-one
<221> NAME/KEY: misc_feature
<222> LOCATION: 6
<223> OTHER INFORMATION: where n is 6H,8H-3,4-dihydropyrimido[4,5-c][1,
2]oxazin-7-one
<221> NAME/KEY: misc_feature
<222> LOCATION: 9
<223> OTHER INFORMATION: where n is 6H,8H-3,4-dihydropyrimido[4,5-c][1,
2]oxazin-7-one
<221> NAME/KEY: misc_feature
<222> LOCATION: 12
<223> OTHER INFORMATION: where n is 2-amino-6-methoxyaminopurine
<221> NAME/KEY: misc_feature
<222> LOCATION: 15
<223> OTHER INFORMATION: where n is 6H,8H-3,4-dihydropyrimido[4,5-c][1,
2]oxazin-7-one
<221> NAME/KEY: misc_feature
<222> LOCATION: 18
<223> OTHER INFORMATION: where n is 6H,8H-3,4-dihydropyrimido[4,5-c][1,
2]oxazin-7-one
<221> NAME/KEY: misc_feature
<222> LOCATION: 21
<223> OTHER INFORMATION: where n is 6H,8H-3,4-dihydropyrimido[4,5-c][1,
2]oxazin-7-one

<400> SEQUENCE: 6 gtn tgn gan ggn ttn can gtn gg 23

<210> SEQ ID NO 7
<211> LENGTH: 23
<212> TYPE: DNA
<213> ORGANISM: Artificial Sequence
<220> FEATURE:
<223> OTHER INFORMATION: degenerate oligonucleotide
<221> NAME/KEY: misc_feature
<222> LOCATION: 3
<223> OTHER INFORMATION: where n is 2-amino-6-methoxyaminopurine
<221> NAME/KEY: misc_feature
<222> LOCATION: 6
<223> OTHER INFORMATION: where n is 6H,8H-3,4-dihydropyrimido[4,5-c][1,
2]oxazin-7-one
<221> NAME/KEY: misc_feature
<222> LOCATION: 9
<223> OTHER INFORMATION: where n is 6H,8H-3,4-dihydropyrimido[4,5-c][1,
2]oxazin-7-one
<221> NAME/KEY: misc_feature
<222> LOCATION: 12
<223> OTHER INFORMATION: where n is 6H,8H-3,4-dihydropyrimido[4,5-c][1,
2]oxazin-7-one
<221> NAME/KEY: misc_feature
<222> LOCATION: 15
<223> OTHER INFORMATION: where n is 6H,8H-3,4-dihydropyrimido[4,5-c][1,
2]oxazin-7-one
<221> NAME/KEY: misc_feature
<222> LOCATION: 18
<223> OTHER INFORMATION: where n is 6H,8H-3,4-dihydropyrimido[4,5-c][1,
2]oxazin-7-one
<221> NAME/KEY: misc_feature
<222> LOCATION: 21
<223> OTHER INFORMATION: where n is 6H,8H-3,4-dihydropyrimido[4,5-c][1,
2]oxazin-7-one

<400> SEQUENCE: 7 gtn tgn gan ggn ttn can gtn gg 23

<210> SEQ ID NO 8
<211> LENGTH: 23
<212> TYPE: DNA
<213> ORGANISM: Artificial Sequence
<220> FEATURE:

-continued

<223> OTHER INFORMATION: degenerate oligonucleotide
<221> NAME/KEY: misc_feature
<222> LOCATION: 3
<223> OTHER INFORMATION: where n is 6H,8H-3,4-dihydropyrimido[4,5-c][1,
2]oxazin-7-one
<221> NAME/KEY: misc_feature
<222> LOCATION: 6
<223> OTHER INFORMATION: where n is 6H,8H-3,4-dihydropyrimido[4,5-c][1,
2]oxazin-7-one
<221> NAME/KEY: misc_feature
<222> LOCATION: 9
<223> OTHER INFORMATION: where n is 6H,8H-3,4-dihydropyrimido[4,5-c][1,
2]oxazin-7-one
<221> NAME/KEY: misc_feature
<222> LOCATION: 12
<223> OTHER INFORMATION: where n is 6H,8H-3,4-dihydropyrimido[4,5-c][1,
2]oxazin-7-one
<221> NAME/KEY: misc_feature
<222> LOCATION: 15
<223> OTHER INFORMATION: where n is 6H,8H-3,4-dihydropyrimido[4,5-c][1,
2]oxazin-7-one
<221> NAME/KEY: misc_feature
<222> LOCATION: 18
<223> OTHER INFORMATION: where n is 6H,8H-3,4-dihydropyrimido[4,5-c][1,
2]oxazin-7-one
<221> NAME/KEY: misc_feature
<222> LOCATION: 21
<223> OTHER INFORMATION: where n is 2-amino-6-methoxyaminopurine

<400> SEQUENCE: 8 gtn tgn gan ggn ttn can gtn gg 23

<210> SEQ ID NO 9
<211> LENGTH: 23
<212> TYPE: DNA
<213> ORGANISM: Artificial Sequence
<220> FEATURE:
<223> OTHER INFORMATION: degenerate oligonucleotide
<221> NAME/KEY: misc_feature
<222> LOCATION: 3
<223> OTHER INFORMATION: where n is 6H,8H-3,4-dihydropyrimido[4,5-c][1,
2]oxazin-7-one
<221> NAME/KEY: misc_feature
<222> LOCATION: 6
<223> OTHER INFORMATION: where n is 6H,8H-3,4-dihydropyrimido[4,5-c][1,
2]oxazin-7-one
<221> NAME/KEY: misc_feature
<222> LOCATION: 9
<223> OTHER INFORMATION: where n is 6H,8H-3,4-dihydropyrimido[4,5-c][1,
2]oxazin-7-one
<221> NAME/KEY: misc_feature
<222> LOCATION: 12
<223> OTHER INFORMATION: where n is 6H,8H-3,4-dihydropyrimido[4,5-c][1,
2]oxazin-7-one
<221> NAME/KEY: misc_feature
<222> LOCATION: 15
<223> OTHER INFORMATION: where n is 6H,8H-3,4-dihydropyrimido[4,5-c][1,
2]oxazin-7-one
<221> NAME/KEY: misc_feature
<222> LOCATION: 18
<223> OTHER INFORMATION: where n is 6H,8H-3,4-dihydropyrimido[4,5-c][1,
2]oxazin-7-one
<221> NAME/KEY: misc_feature
<222> LOCATION: 21
<223> OTHER INFORMATION: where n is 6H,8H-3,4-dihydropyrimido[4,5-c][1,
2]oxazin-7-one

<400> SEQUENCE: 9 gtn tgn gan ggn ttn can gtn gg 23

<210> SEQ ID NO 10
<211> LENGTH: 25
<212> TYPE: DNA
<213> ORGANISM: Artificial Sequence
<220> FEATURE:

-continued

```
<223> OTHER INFORMATION: oligonucleotide

<400> SEQUENCE: 10

gac cgt tca gct gga tat tac ggc c                                25


<210> SEQ ID NO 11
<211> LENGTH: 13
<212> TYPE: DNA
<213> ORGANISM: Artificial Sequence
<220> FEATURE:
<223> OTHER INFORMATION: consensus sequence for initiation
      of translation by eukaryotic ribosomes

<400> SEQUENCE: 11

gcc gcc rcc aug g                                                13


<210> SEQ ID NO 12
<211> LENGTH: 23
<212> TYPE: DNA
<213> ORGANISM: Artificial Sequence
<220> FEATURE:
<223> OTHER INFORMATION: degenerate oligonucleotide
<221> NAME/KEY: misc_feature
<222> LOCATION: 3
<223> OTHER INFORMATION: where n is 6H,8H-3,4-dihydropyrimido[4,5-c][1,
      2]oxazin-7-one
      or 2-amino-6-methoxyaminopurine
<221> NAME/KEY: misc_feature
<222> LOCATION: 6
<223> OTHER INFORMATION: where n is 6H,8H-3,4-dihydropyrimido[4,5-c][1,
      2]oxazin-7-one
<221> NAME/KEY: misc_feature
<222> LOCATION: 9
<223> OTHER INFORMATION: where n is 6H,8H-3,4-dihydropyrimido[4,5-c][1,
      2]oxazin-7-one
<221> NAME/KEY: misc_feature
<222> LOCATION: 12
<223> OTHER INFORMATION: where n is 6H,8H-3,4-dihydropyrimido[4,5-c][1,
      2]oxazin-7-one
      or 2-amino-6-methoxyaminopurine
<221> NAME/KEY: misc_feature
<222> LOCATION: 15
<223> OTHER INFORMATION: where n is 6H,8H-3,4-dihydropyrimido[4,5-c][1,
      2]oxazin-7-one
<221> NAME/KEY: misc_feature
<222> LOCATION: 18
<223> OTHER INFORMATION: where n is 6H,8H-3,4-dihydropyrimido[4,5-c][1,
      2]oxazin-7-one
<221> NAME/KEY: misc_feature
<222> LOCATION: 21
<223> OTHER INFORMATION: where n is 6H,8H-3,4-dihydropyrimido[4,5-c][1,
      2]oxazin-7-one or 2-amino-6-methoxyaminopurine

<400> SEQUENCE: 12

gtn tgn gan ggn ttn can gtn gg                                   23
```

METHOD FOR ISOLATING AND RECOVERING TARGET DNA OR RNA MOLECULES HAVING A DESIRED NUCLEOTIDE SEQUENCE

CROSS-REFERENCE TO RELATED PATENT APPLICATIONS

This application claims the benefit and is a continuation under 35 U.S.C. §120 of U.S. application Ser. No. 09/103,577, filed on Jun. 24, 1998, now U.S. Pat No. 6,268,133 B1, which claims the benefit under 35 U.S.C. §119(e) of U.S. Provisional Application No. 60/050,729, filed on Jun. 25, 1997, both herein incorporated by reference in their entirety.

FIELD OF THE INVENTION

The invention relates to an improved method for isolating and recovering target DNA or RNA molecules having a desired nucleotide sequence. Specifically, it relates to a method for the rapid isolation of specific nucleic acid target molecules.

BACKGROUND OF THE INVENTION

The ability to clone gene sequences has permitted inquiries into the structure and function of nucleic acids, and has resulted in an ability to express highly desired proteins, such as hormones, enzymes, receptors, antibodies, etc., in diverse hosts.

The most commonly used methods for cloning a gene sequence involve the in vitro use of site-specific restriction endonucleases, and ligases. In brief, these methods rely upon the capacity of the "restriction endonucleases" to cleave double-stranded DNA in a manner that produces termini whose structure (i.e., 3' overhang, 5' overhang, or blunt end) and sequence are both well defined. Any such DNA molecule can then be joined to a suitably cleaved vector molecule (i.e., a nucleic acid molecule, typically double-stranded DNA, having specialized sequences which permit it to be replicated in a suitable host cell) through the action of a DNA ligase. The gene sequence may then be duplicated indefinitely by propagating the vector in a suitable host. Methods for performing such manipulations are well-known (see, for example, Perbal, B. *A Practical Guide to Molecular Cloning,* John Wiley & Sons, NY, (1984), pp. 208–216; Sambrook, J., et al. (In: *Molecular Cloning, A Laboratory Manual,* Cold Spring Harbor Press, Cold Spring Harbor, N.Y. (1982); Old, R. W. et al., In: *Principles of Gene Manipulation,* 2nd Ed., University of California Press, Los Angeles, (1981), all herein incorporated by reference).

In some cases, a gene sequence of interest is so abundant in a source that it can be cloned directly without prior purification or enrichment. In most cases, however, the relative abundance of a desired target DNA molecule will require the use of ancillary screening techniques in order to identify the desired molecule and isolate it from other molecules of the source material.

A primary screening technique involves identifying the desired clone based upon its DNA sequence via hybridization with a complementary nucleic acid probe.

In situ filter hybridization methods are particularly well known (see, Sambrook, J., et al., In: *Molecular Cloning, A Laboratory Manual,* 2nd Ed., Cold Spring Harbor Laboratory Press, Cold Spring Harbor, N.Y. (1989)). In such methods, bacteria are lysed on the surface of the membrane filter and then incubated in the presence of a detectably labeled nucleic acid molecule whose sequence is complementary to that of the desired sequence. If the lysate contains the desired sequence, hybridization occurs and thereby binds the labeled molecule to the adsorbent surface. The detection of the label on the adsorbent surface reveals that the bacteria sampled contained the desired cloned sequence.

Although these screening methods are useful and reliable, they require labor-intensive and time consuming steps such as filter preparation and multiple rounds of filter hybridization and colony platings/phage infections. Generally, these procedures will screen up to $10^6$ colonies effectively, but may take weeks or months to yield the desired clone.

Other approaches have been developed to isolate recombinant molecules which have eliminated the tedious filter-handling procedure. These approaches employ conventional hybridization technology coupled with chromatography or magnetic particle technology. Rigas, B. et al., for example, reported a method for isolating one plasmid species from a mixture of two plasmid species. In the disclosed method, circular double-stranded plasmid DNA is hybridized to a RecA protein-coated biotinylated probe to form a stable triple-stranded complex, which is then selectively bound to an agarose-streptavidin column (Rigas, B. et al., *Proc. Natl. Acad. Sci.* (*U.S.A.*) 83: 9591–9595 (1986)). The method thus permits the isolation of cloned double-stranded molecules without requiring any separation of the strands.

A DNA isolation method, termed "triplex affinity capture," has been described in which a specific double-stranded genomic DNA is hybridized to a biotinylated homopyrimidine oligonucleotide probe to form a "triplex complex," which can then be selectively bound to streptavidin-coated magnetic beads (Ito, T. et al., *Nucleic Acids Res.* 20: 3524 (1992); Ito, T. et al., *Proc. Natl. Acad. Sci.* (*U.S.A.*) 89: 495–498 (1992)). Takabatake, T. et al. have described a variation of this technique that employs a biotinylated purine-rich oligonucleotide probe to detect and recover the desired nucleic acid molecule (Takabatake, T. et al., *Nucleic Acid Res.* 20: 5853–5854 (1992)). A practical drawback with these particular approaches is that they are restricted to isolation of target DNA sequences containing homopurine-homopyrimidine tracts.

Fry, G. et al. discuss a method for sequencing isolated M13-LacZ phagemids (Fry, G. et al., *BioTechniques* 13:124–131 (1992)). In this method, a clone is selected and the phagemid DNA is permitted to hybridize to a biotinylated probe whose sequence is complementary to the phagemid's lacZ region. The biotinylated probe is attached to a streptavidin-coated paramagnetic bead. Since the DNA bound to the bead can be separated from unbound DNA, the method provides a means for separating the cloned sequence from the bacterial sequences that are inevitably present (Fry, G. et al., *BioTechniques* 13:124–131 (1992)).

Still another method of screening recombinant nucleic acid molecules is described by Kwok, P. Y. et al. This method, which is an extension of PCR-based screening procedures uses an ELISA-based oligonucleotide-ligation assay (OLA) to detect the PCR products that contain the target source (Kwok, P. Y. et al., *Genomics* 13: 935–941 (1992)). The OLA employs an "reporter probe" and a phosphorylated/biotinylated "anchor" probe, which is captured with immobilized streptavidin (Landegren, U. et al., *Science* 241:1077–1080 (1988)).

The isolation of target DNA from a complex population using a subtractive hybridization technique has also been described (Lamar, E. E. et al., *Cell* 37:171–177 (1984); Rubenstein, J. L. R. et al., *Nucleic Acids Res.* 18:4833–4842 (1990); Hedrik, S. M. et al., *Science* 308:149–153 (1984);

Duguid, J. R. et al., *Proc. Natl. Acad. Sci.* (*U.S.A.*) 85:5738–5742 (1988)). In such "subtractive hybridization" screening methods, the cDNA molecules created from a first population of cells is hybridized to cDNA or RNA of a second population of cells in order to "subtract out" those cDNA molecules that are complementary to nucleic acid molecules present in the second population and thus reflect nucleic acid molecules present in both populations.

The method is illustrated by Duguid, J. R. et al. (*Proc. Natl. Acad. Sci.* (*U.S.A.*) 85:5738–5742 (1988)) who used subtractive hybridization to identify gene sequences that were expressed in brain tissue as a result of scrapie infection. A cDNA preparation made from uninfected cells was biotinylated and permitted to hybridize with cDNA made from infected cells. Sequences in common to both cDNA preparations hybridized to one another, and were removed from the sample through the use of a biotin-binding (avidin) resin.

Weiland, I. et al. (*Proc. Natl. Acad. Sci.* (*U.S.A.*) 87:2720–2724 (1990)) reported an improved method of subtractive hybridization in which tester DNA was cleaved with a restriction endonuclease, and then permitted to hybridize to sheared driver DNA at high $C_0t$ values ("$C_0t$" is the product of the initial concentration of DNA and the time of incubation). By cloning the double-stranded, PCR-amplified, unique DNA molecules into a plasmid vector, it was possible to obtain an enrichment in the relative proportion of target sequences recovered.

Rubenstein, J. L. R. et al. (*Nucleic Acids Res.* 18:4833–4842 (1990)) reported a further improvement in subtractive hybridization methods that employed single-stranded phagemid vectors to provide both the target and tester DNA. In the method, hybridized phagemid DNA-biotinylated driver strand complexes are separated from unhybridized DNA by the addition of streptavidin. Unhybridized single-stranded DNA was subsequently converted to the double-stranded form using Taq DNA polymerase and an oligonucleotide complementary to a common region found within the single-stranded DNA. The use of this method is, however, limited by the need to follow a rigorous single-stranded phagemid purification protocol in order to obtain a preparation virtually free of contaminant double-stranded DNA (Rubenstein, J. L. R. et al., *Nucleic Acids Res.* 18: 4833–4841 (1990)).

In sum, methods for isolating particular target nucleic acid molecules are restricted by the abundance of the DNA target sequence, and by time-consuming steps. Accordingly, a method that would expedite the isolation of desired target nucleic acid molecules and that could yield essentially pure target DNA would be highly desirable.

SUMMARY OF THE INVENTION

The present invention provides a method for rapidly isolating nucleic acid molecules having a desired nucleotide sequence from other undesired nucleic acid molecules. In particular, the invention allows for isolation of a desired nucleic acid molecule from a population of nucleic acid molecules. Significantly, the present invention further relates to an improved method of screening target nucleic acid molecules employing hybridization methodology combined with ligand separation, DNA repair, and restriction enzyme digestion technology.

In detail, the invention provides a method for selectively isolating a desired target nucleic acid molecule present in an initial sample containing a mixture (or library) of nucleic acid molecules, wherein said method comprises the steps:

(a) (1) where said initial mixture or library is composed of single-stranded nucleic acid molecules, performing step (b); or (2) where said initial mixture or library is composed of double-stranded nucleic acid molecules treating said double-stranded nucleic acid molecules to render such molecules single-stranded, then performing step (b);

(b) incubating single-stranded nucleic acid molecules of said mixture or library in the presence of haptenylated nucleic acid probe molecules, said probe molecules comprising a nucleotide sequence complementary to a nucleotide sequence of said desired target molecule; said incubation being under conditions sufficient to permit said probe molecules to hybridize to said desired target molecules, thereby generating hybridized molecules wherein said desired target molecules are bound to said probe molecules;

(c) capturing said hybridized molecules of step (b) by incubating said hybridized molecules in the presence of a binding ligand of the hapten of said haptenylated probes, said binding ligand being conjugated to a support; said incubation being sufficient to permit said hybridized molecules to become bound to said binding ligand of said support;

(d) separating said bound hybridized desired target molecules from unbound nucleic acid molecules; and (e) recovering said desired target molecules from said support.

In a preferred embodiment, the invention concerns the use of one or more amino acid denaturants for separating double-stranded nucleic acid molecules. Such amino acid denaturants allow separation of complementary strands of double stranded nucleic acid molecules formed by hybridization. In particular these amino acid denaturants provide separation of the double-stranded nucleic acid molecule mixture prior to hybridization with the haptenylated nucleic acid probes (step (a)) and preferably are used to separate the probes from the desired nucleic acid molecule. In a particularly preferred embodiment of the invention, the desired nucleic acid molecules are recovered by incubating the support containing the bound probes hybridized to the desired molecules with one or more amino acid denaturants. Such incubation is carried out under conditions sufficient to release the desired molecules from the probes.

According to the invention, an amino acid denaturant includes any amino acid, polyamino acid or derivative thereof which can be used to dissociate or denature double stranded nucleic acid molecules. Such amino acid denaturants include, but are not limited to, glycine, alanine, arginine, asparagine, glutamine, isoleucine, leucine, methionine, phenylalanine, proline, serine, threonine, tryptophan, tyrosine, valine and imidazole.

Thus, the method of the present invention is more particularly directed to recovering one or more desired target nucleic acid molecules from a sample comprising:

(a) contacting said sample in the presence of one or more haptenylated nucleic acid probes comprising a nucleotide sequence complementary to said desired target molecules under conditions sufficient to permit said probes to hybridize to said desired target molecules thereby forming one or more hybridized molecules;

(b) contacting said hybridized molecules with binding ligands conjugated to a support under conditions sufficient to permit said hybridized molecules to become bound to said binding ligands of said support; and (c) contacting said support with one or more amino acid denaturants under conditions sufficient to isolate said desired nucleic acid molecules from said support.

This method of the invention may further comprise:

(d) contacting said isolated desired nucleic acid target molecules with one or more primers complementary to one or more sequences of the desired target nucleic acid molecules under conditions sufficient to generate one or more double-stranded desired nucleic acid target molecules; and (e) transforming said double-stranded desired target molecules into one or more host cells.

In this aspect of the invention, the double-stranded desired target molecule may be produced by incubating the desired target molecules with one or more primers, one or more nucleotides, and a polypeptide having polymerase activity. Such polypeptides having polymerase activity include well known DNA and/or RNA polymerases, preferably thermostable DNA polymerases. Nucleotides for use in this embodiment include but are not limited to dATP, dGTP, dCTP, dTTP, ATP, GTP, CTP, UTP, and analogs thereof. In particular, nucleotide analogs that confer nuclease or endonuclease resistance to the synthesized nucleic acid molecule are particularly preferred. When such nucleotide analogs are used in accordance with the invention, the methods of the invention may further comprise incubating the double-stranded desired target molecule (which contains one or more nucleotide analogs) with one or more nucleases or endonucleases prior to transformation. Incubating such molecules in this manner provides for an additional selection step against contaminating nucleic acid molecules which do not contain such nucleotide analogs. The present invention also concerns the use of unique primers which recognize and hybridize to the desired target nucleic acid molecules. Such primers include sequences which are complementary to the same sequence recognized by the probe molecule or may be complementary to a different sequence within the target nucleic acid molecules. In particularly preferred embodiments, the probes and/or primers are degenerate oligonucleotides, preferably degenerate oligonucleotides which contain one or more universal nucleotides.

The present invention also relates to a method for selecting or enriching for desired target nucleic acid molecules having larger or longer segments from a population of desired target nucleic acid molecules. As will be appreciated, selection of desired nucleic acid molecules in accordance with the invention provides a population of desired molecules which hybridize to the probe. In such a population, the length or size of the sequence contained in each target nucleic acid molecule may vary. In the enrichment method of the invention, the desired nucleic acid molecules having larger segments or larger sequences can be selected by separating the desired nucleic acid molecules according to size. Such size separation can be accomplished by well known techniques including gel electrophoresis (e.g., agarose or acrylamide). Upon separation, larger nucleic acid molecules can be isolated and then utilized for further processing.

In a particular preferred aspect, the enrichment procedure is used to screen cDNA molecules contained in a vector. In such a procedure, the cDNA molecules prepared from messenger RNA or polyA+ RNA are cloned into a vector, thereby forming a cDNA library. Given that the vector is a constant size, selection of larger molecules from the library provides for vectors containing the largest cDNA inserts. In this manner, larger or full length cDNA molecules may be isolated from the cDNA library. This aspect of the invention thus provides a means to select full length desired genes from a cDNA library. In a preferred enrichment method of the invention, the desired target molecules within the cDNA library are amplified prior to size separation.

Thus the invention specifically relates to enrichment of desired nucleic acid molecules having larger or full length inserts comprising:

(a) obtaining a cDNA library;

(b) (1) where said library is composed of single-stranded nucleic acid molecules, performing step (c); or (2) where said library is composed of double-stranded nucleic acid molecules treating said double-stranded nucleic acid molecules to render such molecules single-stranded, then performing step (c);

(c) contacting single-stranded nucleic acid of said library with one or more haptenylated nucleic acid probes comprising a nucleotide sequence complementary to a nucleotide sequence of one or more desired target molecules;

(d) isolating said desired target molecules;

(e) amplifying said isolated desired target molecules; and (f) separating said amplified molecules according to size.

Of course, the enrichment method of the invention may be used on any nucleic acid populations, not only cDNA libraries. In such a method, the population of nucleic acid molecules (preferably contained in a vector) are used to select a subpopulation of desired target nucleic acid molecules. The subpopulation of desired nucleic acid molecules (each molecule likely having a different size) are then separated according to size, preferably after amplification. In the enrichment methods of the invention, regardless of the sample used (cDNA library or other nucleic acid populations), the type and number of probes used for amplification may vary.

DESCRIPTION OF THE PREFERRED EMBODIMENTS

Figure 1:
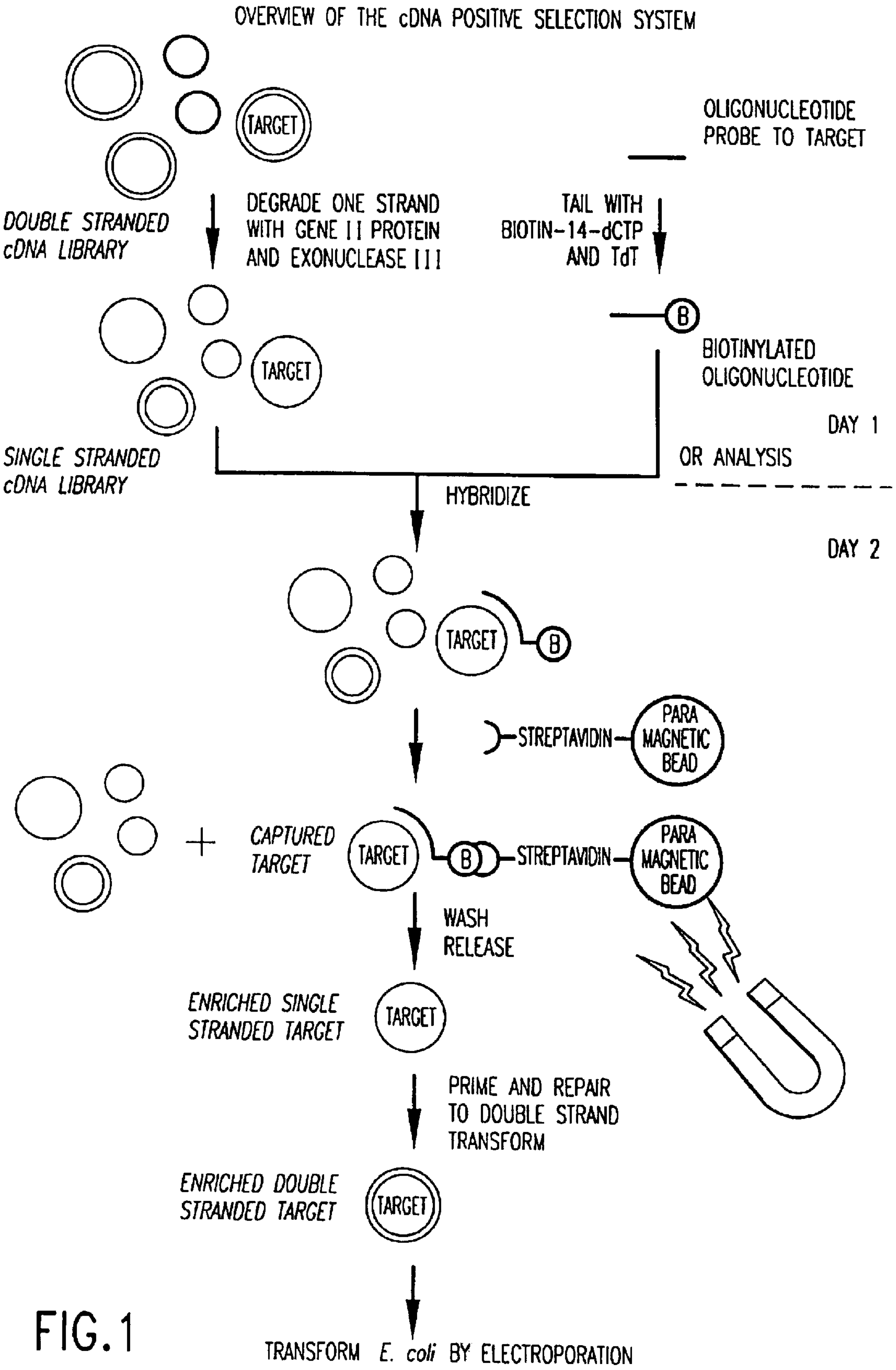
FIG. 1 provides a diagrammatic illustration of a preferred embodiment of the isolation method of the present invention.
Figure 2:
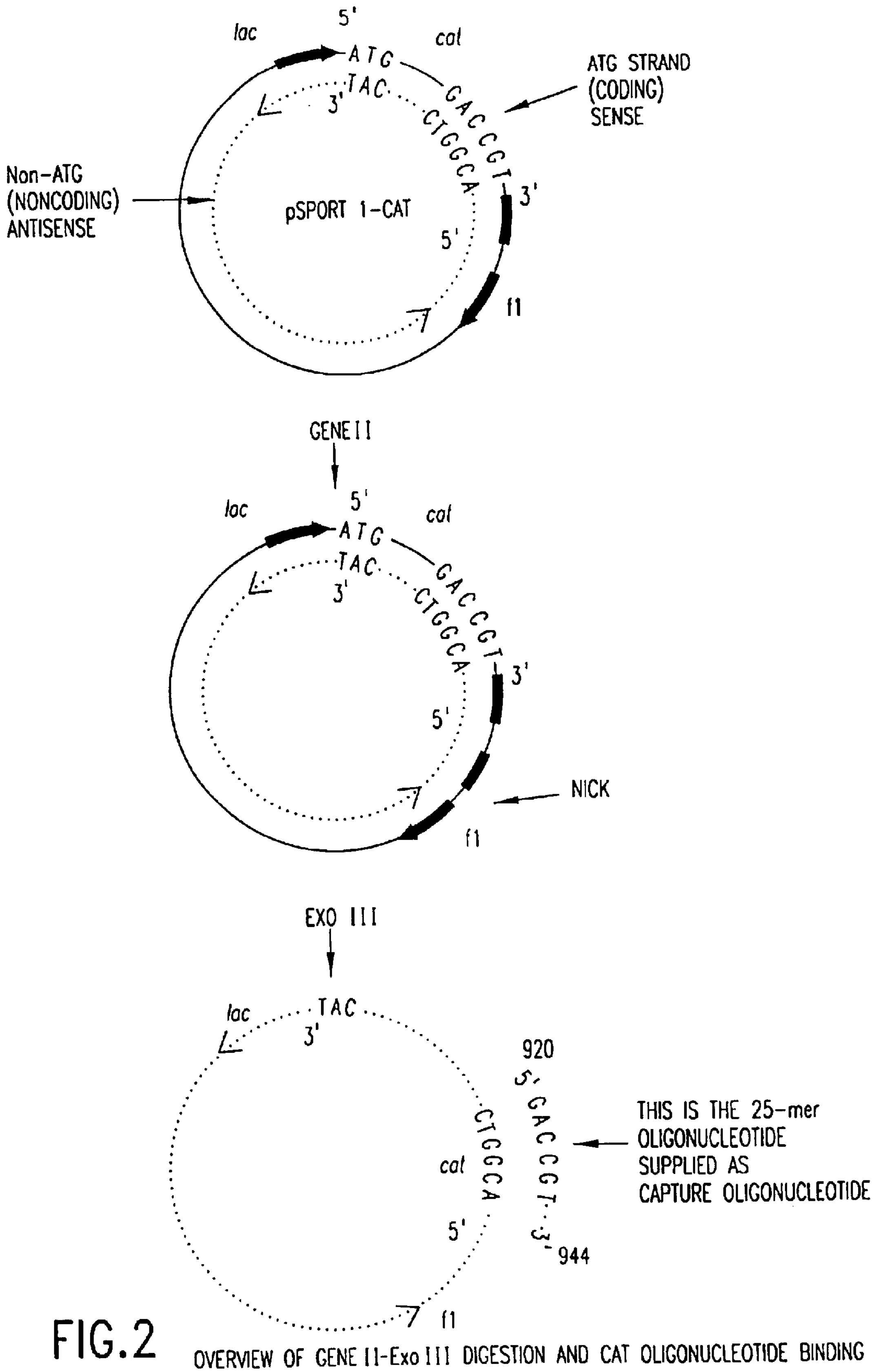
FIG. 2 provides a diagrammatic view of a preferred method for generating single-stranded nucleic acid molecules.

The present invention concerns an improved method for rapidly isolating a "desired" nucleic acid "clone" from a mixture (or library of cloned molecules). The "clones" of the present invention comprise circular or linear DNA or RNA molecules that may be either single-stranded or double-stranded. Typically, such clones or libraries will comprise plasmids or other vectors (such as viral vectors) that have been engineered to contain a "desired" fragment of DNA or RNA derived from a source such as a homogeneous specimen (such as cells in tissue culture, cells of the same tissue, etc.), or a heterogeneous specimen (such as a mixture of pathogen-free and pathogen-infected cells, a mixture of cells of different tissues, species, or cells of the same or different tissue at different temporal or developmental stages, etc.). The cells, if any, of these nucleic acid sources may be either prokaryotic or eukaryotic cells (such as those of animals, humans and higher plants).

Various libraries can be selected for large scale preparation. The construction of plasmid, cosmid, and phagemid cDNA libraries, or genomic libraries are described in Sambrook, J. et al. (In: Molecular Cloning, A Laboratory Manual, 2nd Ed., Cold Spring Harbor Laboratory Press, Cold Spring Harbor, N.Y. (1989), herein incorporated by reference). Preferably, single-stranded phagemid cDNA libraries can be prepared as described previously by Gruber, C. E. et al., (*Focus* 15:59–65 (1993), herein incorporated by reference). The general steps of the method will differ depending upon whether the desired sequence has been cloned into single-stranded or double-stranded molecules, and whether such molecules are DNA or RNA.

As used herein, there is no constraint as to the sequence of the target nucleic acid molecule whose isolation is desired. Since the present invention relies upon nucleic acid hybridization, the target molecules should have a length of at least 10 nucleotides in order to be efficiently recovered. No upper limit to the size of the molecules exists, and the methods of the invention can be used to isolate nucleic acid molecules of several kilobases or more.

The selection method of the present invention is based in part upon the observation that double-stranded nucleic acid molecules transform bacterial cells with greater efficiency than single-stranded nucleic acid molecules. In one embodiment, the invention achieves the isolation of a desired nucleic acid sequence from a library of sequences by providing a primer molecule to the mixture. A "primer" or "primer molecule" as used herein is a single-stranded oligonucleotide or a single-stranded polynucleotide that can be extended by the covalent addition of nucleotide monomers during the template-dependent polymerization reaction catalyzed by a polymerase. A primer is typically 11 bases or longer; most preferably, a primer is 17 bases or longer. However, the primer may range in size from 16 to 300 bases, preferably 16 to 32 bases and most preferably 20 to 24 bases. Examples of suitable DNA polymerases include the large proteolytic fragment of the DNA polymerase I of the bacterium *E. coli,* commonly known as "Klenow" polymerase, *E. coli* DNA polymerase I, the bacteriophage T7 DNA polymerase. Preferably, a thermostable polymerase will be used, such as a polymerase that can catalyze nucleotide addition at temperatures of between about 50° C. to about 100° C. Additionally, combinations of polymerases may be used to increase the efficiency of polymerization, such as Elongase (Life Technologies, Inc., Gaithersburg, Md.). Exemplary thermostable polymerases are described in European Patent Application No. 0258017, incorporated herein by reference. The thermostable "Taq" DNA polymerase (Life Technologies, Inc., Gaithersburg, Md.) is an example, although other well known thermostable polymerases and their mutants and derivatives thereof may be used, such as Tne DNA polymerase (WO96/10640, copending application Ser. No. 08/706,706, filed Sep. 6, 1996 and copending application 60/037,393, filed Feb. 7, 1997), Tma DNA polymerase (U.S. Pat. No. 5,374,553), Pfu DNA polymerase (U.S. Pat. No. 5,489,523), Vent DNA polymerase (U.S. Pat. Nos. 5,210,036, 5,500,363, 5,352,778, and 5,322,785), DEEPVENT® (New England Biolabs), Dynazyme (Finnzymes, Finland), and Tfl (Epicenter Technologies, Inc.).

Where the target mixture involved RNA molecules, and a DNA molecule is desired, a reverse transcriptase may be employed. Reverse transcriptases are discussed by Sambrook, J. et al. (In: *Molecular Cloning: A Laboratory Manual,* Cold Spring Harbor Laboratory Press, Cold Sparing Harbor, N.Y. (1989)) and by Noonan, K. F. et al. (*Nucleic Acids Res.* 16:10366 (1988)). Preferably, reverse transcriptases substantially lacking RNase H activity (U.S. Pat. No. 5,244,797) are used. Such reverse transcriptases may be obtained from Life Technologies, Inc. (Gaithersburg, Md.). Similarly, where the target mixture comprises RNA, an RNA polymerase may be used. Examples of suitable RNA polymerases include *E. coli* RNA polymerase, T7 RNA polymerase, etc.

As a consequence of such polymerization, the desired target molecules, but not other nucleic acid molecules of the mixture, are converted into a double-stranded form. The mixture can, without further processing, be transformed into suitable recipient bacteria (see, Sambrook, J. et al., In: Molecular Cloning: A Laboratory Manual, Cold Spring Harbor Laboratory Press, Cold Spring Harbor, N.Y. (1989)). Transformants can be recovered, and their recombinant DNA or RNA molecules can be extracted and retrieved. Such processing provides a new mixture or library of nucleic acid molecules that is substantially enriched for the desired molecules. Optionally, the above-described method can be repeated (as often as desired) in order to obtain mixtures or libraries that are more highly enriched for the desired nucleic acid sequence.

A preferred method for conducting such processing employs a library or mixture of a single-stranded phagemid, such as M13, or from vectors such as pSPORT 1, pCMV•SPORT (particularly DNA cloned into the Not I-Sal I region), pZL1 (λZiplox®), P1, PAC, YAC, BAC and BlueScript SK (+). In a preferred embodiment of the method, a primer is used to convert the single-stranded DNA molecule into a double-stranded form. When using a single-stranded phagemid vector, care must be taken to select an oligonucleotide with the correct polarity. If the target gene is cloned into multiple cloning sites in the same orientation as the lacZ gene, sense strand (i.e., the strand containing the ATG initiation codon for protein synthesis) sense oligonucleotides need to be used to capture ssDNA produced from vectors such as pSPORT 1, pCMV●SPORT (particularly DNA cloned into the Not I-Sal I region), pZL1 (and BlueScript SK (+). Anti-sense (non-ATG stand) oligonucleotides are used to capture ssDNA produced from vectors such as pSPORT2, BlueScript SK (−), and λZap®II. If ssDNA is generated by in vivo phagemid production, oligonucleotide of the reverse polarity must be designed (i.e., anti-sense oligonucleotides for pSPORT 1, pCMV●SPORT, etc.).

A highly preferred embodiment of the present invention is marketed by Gibco BRL (GeneTrapper™ cDNA Positive Selection System, Life Technologies, Inc. (Gaithersburg, Md.), the instruction manual of which is herein incorporated by reference in its entirety). Also incorporated by reference in its entirety is U.S. Pat. No. 5,500,356 to Li et al. regarding a method of nucleic acid sequence selection. This embodiment of the present invention facilitates the rapid (1 to 2 days) isolation of cDNA clones from DNA prepared from a cDNA library (representing, for example, $10^{12}$ DNA molecules) with no prior cDNA library screening. In this system (FIG. 1), an oligonucleotide, complementary to a segment of the target cDNA, is biotinylated at the 3' end with biotin-14-dCTP using terminal deoxynucleotidyl transferase ("TdT"). Simultaneously, a complex population of double-stranded phagemid DNA containing cDNA inserts (e.g., $10^6$ to $10^7$ individual members) is converted to single-stranded DNA ("ssDNA") using Gene II (phage F1 endonuclease) and (*E. coli*) Exonuclease III (Exo III). Hybrids between the biotinylated oligonucleotide and ssDNA are formed in solution and are then captured on streptavidin-coated paramagnetic beads. A magnet is used to retrieve the paramagnetic beads from solution, leaving nonhybridized ssDNA behind in solution. Subsequently, the captured ssDNA target is released from the biotinylated oligonucleotide that remains attached to the paramagnetic beads. After release, the desired cDNA clone is further enriched by using a non-biotinylated target oligonucleotide to specifically prime conversion of the recovered ssDNA target to double stranded DNA ("dsDNA"). The term "repair" as used herein refers to the conversion of ssDNA into dsDNA. Following transformation and plating, typically, 20% to 100% of the colonies represent the cDNA done of interest. If the percent representation of the target cDNA species is unknown, the repair step is preferably used to ensure adequate enrichment of the target cDNA.

The GeneTrapper™ System provides several distinct advantages over PCR (GeneTrapper™ cDNA Positive Selection System, Life Technologies, Catalog No. 10356-020, herein incorporated by reference in its entirety). Cloned, full-length cDNAs can be easily isolated by using the GeneTrapper™ System and one specific oligonucleotide of ≧16 nucleotides that is designed to anneal to the 5' coding region. To obtain the same result from PCR would require sequence information at the 5' and 3' regions of the desired cDNA (two oligonucleotides) or a more difficult combined 3'-5' procedure followed by a cloning procedure.

Oligonucleotide probes designed to the sequence information as close to the 5'-terminus of the target nucleic acid molecule will tend to enrich for full-length cDNA clones. On the other hand, oligonucleotides containing sequences proximal to the 3'-terminus of the original mRNA will select partial, full-length, and all other related cDNA clones (i.e., spliced transcripts).

In accordance with the invention, the GeneTrapper system may be modified by one or a combination of improvements including (1) utilizing degenerate oligonucleotides (particularly oligonucleotides containing universal nucleotides such as dP and/or dK) as primers and/or as haptenylated probes, (2) utilizing one or more amino acid denaturants to convert the double-stranded nucleic acid molecules into single-stranded nucleic acid molecules, (3) utilizing nucleotide analogs during the repair reaction to confer nuclease resistance; and (4) enrichment of larger or full-length nucleic acid molecules.

A. Capture Enrichment of Desired Molecules

The selection method of the present invention employs a nucleic acid "capture" step. This embodiment is preferably performed using single-stranded nucleic acid molecules. Where double-stranded circular molecules are employed, a preferred initial step involves denaturing (or otherwise separating) the molecules into their respective single strands. Such denaturation may be accomplished by transient incubation of the sample at elevated temperatures (60–80° C. or above the Tm of the mixture), or preferably by the use of one or more amino acid denaturants. Alternatively, salt or ionic conditions can be adjusted, or denaturation can be accomplished via helicase activity. The strand-separation step may require a topoisomerase in order to permit full strand separation. Alternatively, the double-stranded plasmid or linear target DNA could be nicked and the nicked strand removed by denaturation or digestion.

A preferred method for accomplishing such nicking and strand removal involves employing double-stranded circular molecules that contain a region of an origin of replication of an isometric or filamentous bacteriophage. Isometric bacteriophage include ϕX174, G4, G13, S13, St-1, ϕK, U3, G14, α3 and G6. Filamentous bacteriophage include f1, fd, M13, If1, and Ike. Origin regions of M13 and fd are preferred (Baas, P. D. et al., *Curr. Top. Microbiol. Immunol.* 136:31–70 (1988); Baas, P. D., *Biochim. Biophys. Acta* 825:111–139 (1985), both herein incorporated by reference).

Various bacteriophage proteins, and in particular, the Gene II protein of fd, and its analogs, can cleave a specific site in the region of an origin of replication of an isometric bacteriophage. Thus, by incubating such proteins with a double-stranded circular molecule that contains an isometric bacteriophage origin of replication region, it is possible to nick one strand of the circular molecule (Meyer, T. F. et al., *Nature* 278:365–367 (1979) herein incorporated by reference). By further incubating the nicked molecule in the presence of an exonuclease (such as Exonuclease III), it is possible to degrade the nicked strand and obtain a preparation of circular single-stranded molecules (Chang, D. W. et al., *Gene* 127:95–98 (1993); Eastlake, P. B. et al., PCT Application No. WO95/09915, both herein incorporated by reference). Gene II-Exo III prepared ssDNA is in the opposite polarity to ssDNA generated by in vivo phagemid production.

In another aspect of the invention, the double-stranded molecules (preferably double-stranded circular molecules) are denatured by contacting the double-stranded molecules with one or more amino acid denaturants. Such amino acid denaturants includes any amino acid, polyamino acid, or derivative thereof which can be used to dissociate or denature double-stranded nucleic acid molecules. Such amino acids comprise one or more amino acids selected from the group consisting of alanine, arginine, asparagine, aspartic acid, cysteine, glutamine, glutamic acid, glycine, histidine, imidazole, isoleucine, leucine, lysine, methionine, ornithine, phenylalanine, proline, serine, threonine, tryptophan, tyrosine, valine and derivatives or analogs thereof; although, glycine, alanine, arginine, asparagine, glutamine, isoleucine, leucine, methionine, phenylalanine, proline, serine, threonine, tryptophan, tyrosine, valine, imidazole, and derivatives or analogs thereof are preferred. Polyamino acids comprise two or more of such amino acids as well as their derivatives or analogs thereof. In accordance with the invention, any number of amino acids (and derivatives or analogs thereof) may be combined with any number of polyamino acids (and derivatives or analogs thereof) to denature double-stranded nucleic acid molecules. In the method of the invention, the amino acid denaturants allow for separation or denaturation of the double-stranded nucleic acid molecules to form single-stranded molecules. Contrary to the strand removal method (above), amino acid denaturants produce single-stranded molecules representing both strands of the double-stranded nucleic acid molecules. Preferably, amino acid denaturants are provided in a solution or as a buffer. The concentration of the amino acid denaturants in such buffers or solutions which is sufficient to denature or dissociate the double-stranded DNA molecule may be easily determined by one of ordinary skill in the art, taking in the consideration the amount and size of the double-stranded molecules. Typically, amino acid denaturants are used at a concentration from 1–500 mM, preferably 1–100 mM, more preferably 1–50 mM, still more preferably 5–50 mM, and most preferably 10–30 mM.

In accordance with the present invention, the population of single-stranded molecules is then incubated in the presence of one or more oligonucleotide probes under conditions sufficient to permit and promote sequence-specific nucleic acid hybridization. Hybridization may be conducted under conditions which either permit or minimize random hybridization. As used herein, conditions which minimize random hybridization are of such stringency that they permit hybridization only of sequences that exhibit complete complementarity. In contrast, conditions that permit random hybridization will enable molecules having only partial complementarity to stabily hybridize with one another. Suitable conditions which either permit or minimize random nucleic acid hybridization are described by Sambrook, J., et al. (In: Molecular Cloning, A Laboratory Manual, Cold Spring Harbor Laboratories, Cold Spring Harbor, N.Y. (1982)); Haymes, B. D., et al. (In: Nucleic Acid Hybridization, A Practical Approach, IRL Press, Washington, D.C. (1985), both herein incorporated by reference), and similar texts.

The probe is a nucleic acid molecule, preferably DNA, preferably greater than 8–12 nucleotides in length, and most preferably greater than 15–30 nucleotides in length, whose sequence is selected to be complementary to the sequence of a region of the target molecule that is to be isolated. However, the probe may range from 16 to 300 bases, preferably 16–32 bases and most preferably 20–24 bases. The probe thus need not be, and most preferably will not be equal in size to the target molecule that is to be recovered. The oligonucleotide probe will, preferably have G+C content of from about 50% to about 60%. A higher G+C content will increase the number of background colonies.

Two sequences are said to be "complementary" to one another if they are capable of hybridizing to one another to form a stable anti-parallel, double-stranded nucleic acid structure. Thus, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization to form a double-stranded structure. However, complementarity determines the specificity of the capture reaction.

In one embodiment, the probe (and/or primer) may contain nucleotide analogues that are capable of hybridizing to more than one species of the four naturally occurring deoxynucleotides (dC, dG, dT, and dA). 2'-deoxylnosine or 2'-deoxyNebularine which exhibit low, but unequal, hydrogen bonding to all four bases may be employed for such purpose. Alternatively, a "universal nucleotide" may be employed. In this strategy, the base analog does not hybridize significantly to any of the four bases. 3-Nitropyrrole 2'-deoxynucleoside, and 5-nitro-indole are examples of such universal bases (Nichols, R. et al., *Nature* 369:492–493) (1994); Loakes, D. et al., *Nucl. Acids Res.* 22:4039–4043 (1994)). Nucleotides having bases capable of hybridizing to multiple species of nucleotide, as well as "universal nucleoside" may be obtained from Glen Research (Lin et al., *Nucleic Acids Res.* 17:10373–10383 (1989); and Lin et al. *Nucleic Acids Res.* 20:5149–5152(1992)). Examples of such universal nucleotide include dP and dK, obtainable from Glen Research. Throughout this specification, dP is a deoxynbonucleotide wherein the nucleotide base P represents 6H,8H-3,4-dihydropyrimido[4,5-c][1,2]oxazin-7-one. Throughout this specification, dK is a deoxyribonucleotide wherein the nucleotide base K represents 2-amino-6-methoxyaminopurine. When used in a sequence, dP is interchangeable with P, and dK is interchangeable with K.

Additionally, the probes (and/or primers) used in accordance with the invention may be protein nucleic acids (PNA's) (U.S. Pat. No. 5,539,082, herein incorporated by reference). Use of such protein nucleic acids may allow for increased strength of binding of the probe (and/or primer) to the nucleic acid molecule.

In another embodiment, the sequence of the probe (and/or the primer) may be derived from amino acid sequence data. In these instances, the probe (and/or the primer) may have a degenerate sequence. For instance, if one had an amino acid motif (e.g., zinc fingers) that occurred in a number of proteins encoded in a library, one could enrich for nucleic acids encoding proteins having that motif. By designing the oligonucleotide probe to the amino acid encoding region of the cDNA, the capture of vector sequences will be avoided.

In a preferred sub-embodiment, the probe is "haptenylated." As used herein, a "haptenylated" probe is a nucleic acid molecule that has been covalently bonded to one or more of the same or different hapten molecules. A hapten is a molecule that can be recognized and bound by another molecule, e.g., a ligand. Examples of haptens include any antigen, biotin, dinitrophenol, etc. Biotin is a preferred hapten of the present invention and may be bound by proteins such as avidin and streptavidin.

The probe may be "haptenylated" using any of a variety of methods well known in the art. Methods for "biotinylating" the probe are described, for example, by Hevey et al. (U.S. Pat. No. 4,228,237); Kourilsky et al. (U.S. Pat. No. 4,581,333); Hofman et al. (*J. Amer. Chem. Soc.* 100:3585–3590 (1978)); Holmstrom, K. et al. (*Anal. Biochem.* 209:278–283 (1993)); etc. Such modification is most preferably accomplished by incorporating biotinylated nucleotides into a nucleic acid molecule using conventional methods. Alternatively, such modification can be made using photobiotin (Vector Laboratories). Other methods can, of course, be employed to produce such biotinylated molecules.

The formation of dimers or hairpin structure at the 3' terminus of the oligonucleotide probe will reduce or eliminate the ability of TdT to add biotin to the oligonucleotide. To avoid hairpin formation, oligonucleotide programs such as OLIGO™ 4.0 or OLIGO™ 5.0 for Windows may be used to design the oligonucleotide probe.

In a highly preferred method, a single biotinylated nucleotide species is employed (e.g., biotinylated dCTP), and the nucleotide is incorporated into the probe molecule either throughout the length of the probe, or, more preferably, at an end of the probe, such that a homopolymeric region is created (e.g., poly-biotinylated dC).

The above-described incubation thus results in the hybridization of the haptenylated probe and the desired target sequence such that a hybridized molecule having a double-stranded region is formed.

Simultaneously, or in the next step of the preferred method, this complex is "captured" using a hapten binding ligand molecule that has been bound to a solid support. Suitable hapten binding ligands include anti-hapten antibody (or antibody fragments), hapten receptor, etc. The choice of ligand will vary with the particular hapten employed. For example, when biotin is employed as the hapten, the hapten binding ligand is preferably avidin, streptavidin, or antibody or antibody fragments that bind biotin. Where the probe contains a homopolymeric region (e.g., poly-biotinylated dC), it is preferable to add a "counter-probe" of complementary sequence (e.g., where the probe has a poly-biotinylated dC homopolymeric region, the counter-probe may be a nucleic acid molecule having a poly-dG or poly-dC region). The addition of the counter-probe is optional, and serves to reduce the background extent to which undesired sequences are recovered. The use of such counter-probe is thus desirable when the level of undesirable species recovered by the probe is considered unacceptable.

Suitable solid supports include, but are not limited to, beads, tubes, or plates, which may be made of materials including, but not limited to, latex, glass, polystyrene, polypropylene, or other plastic. Such supports can be 2-dimensional strips, beads, etc. A preferred support is a magnetic or paramagnetic bead (Seradyn, Indianapolis, Ind.). In a preferred sub-embodiment, the capture of the hybridized haptenylated probe is initiated without the necessity for removing non-hybridized molecules.

Methods for effecting the attachment of the hapten binding ligand to the support are described by Hevey et al. (U.S. Pat. No. 4,228,237) and by Kourilsky et al. (U.S. Pat. No. 4,581,333). When a biotin hapten is employed, a paramagnetic-streptavidin conjugated bead, obtained from Life Technologies, Inc. (Gaithersburg, Md.) or the Dynabead Streptavidin is M-280 beads obtained from Dynal (Great Neck, N.Y.) can be used as the ligand and support.

The addition of the beads (or other support) to the reaction permits the haptenylated probe to bind to the hapten-binding ligand of the support. Such binding reactions are very strong. For example, the binding constant for the reaction between avidin and biotin is approximately 1,015 l/mole. The very strong nature of this bond has been found to persist even when biotin is conjugated, by means of its carboxyl group, to another molecule, or when avidin is attached to another molecule.

As a consequence of such binding, any haptenylated probe that has hybridized to a desired target molecule will become bound to the support. In contrast, non-target molecules will remain unbound, and can be separated from the bound material by washing, filtration, centrifugation, sieving, or (in the case of paramagnetic or magnetic supports) by magnetic separation methods.

Most preferably, however, paramagnetic beads are used as the support, and a magnet is used to pull the paramagnetic beads out of solution, and the beads are washed with a suitable buffer (such as one containing Tris, EDTA, and NaCl). Such treatment removes the majority of non-target nucleic acid sequences that were originally present, and hence eliminates undesired non-selected single-stranded nucleic acid molecules from the reaction.

The specifically captured single-stranded target nucleic acid molecules (hybridized to the haptenylated probe) is then released from the probe by one or a combination of treatments, such as addition of an alkaline buffer, addition of one or more amino acid denaturants, heat, etc. Preferably, one or more amino acid denaturants or combinations thereof are used to release the nulceic acid molecules from the support bound probe. The releasing treatment is preferably selected such that the haptenylated probe remains attached to the support. The desired released target molecules are then isolated and may be subject to further selection. Such further selection may include additional probe hybridizations with one or more probes (the same or different than the probes used in the initial selection).

Note that the hapten need not be covalently coupled to the probe-nucleic acid. The hapten may be linked, either covalently or non-covalently, to a molecule that non-covalently binds the probe molecule, e.g., a single-stranded DNA binding protein. The binding protein must bind tightly enough that significant quantities of it will not become disassociated from the probe molecules and bind to nucleic acid molecules of the sample.

This aspect of the present invention permits the recovery of a desired nucleic acid species from a mixture of nucleic acid molecules (i.e., from a target mixture). The target mixture contemplated by the present invention will generally have more than 100 members, and typically more than 1,000, or even 10,000 members, 100,000 members or more. The methods of the present invention are thus capable of recovering a desired member of a target mixture even when such desired member is present at a concentration of less that 1%, 0.1%, 0.01%, 0.001%, 0.0001% or less (percentages are the ratio of the desired species per total number of different species present in the mixture).

B. Enrichment/Selection of Larger or Full Length Desired Molecules

In another preferred embodiment, larger or full-length desired nucleic acid molecules from a population of molecules may be obtained using the process of the invention. Thus, the invention provides a method to first select for desired target molecules (e.g., genes or gene fragments) and then allows for selection of larger or full-length target molecules (e.g., full-length genes). In this aspect of the invention, the subpopulation of desired nucleic acid molecules are separated according to size.

In accordance with the invention, size selection may be accomplished by standard gel electrophoresis techniques (agarose or acrylamide gel electrophoresis) and the larger or full-length molecules may be extracted from the gel. In a preferred aspect of the invention, prior to separation by size, the nucleic acid molecules are amplified by well known amplification techniques.

In one embodiment, the subpopulation of target nucleic acid molecules are contained in a vector which facilities amplification of the nucleic acid molecules inserted into the vector. Such amplification may be accomplished by contacting the subpopulation of target nucleic acid molecules with a first probe which hybridizes to a portion of the vector and a second probe which hybridizes to a portion of the vector insert. Depending on the location of the probes used, amplification of either the 5' or the 3' portions of vector inserts in the population is accomplished. Upon separation by size, the invention thus provides enrichment for molecules having longer segments at the 5' or 3' terminus. Such longer segments may then be used to re-create or construct longer or full-length gene segments. For example, the 5' or the 3' larger segment may be sub-cloned to replace a shorter segment in a vector containing a desired nucleic acid molecule. Such replacement may be accomplished by well known restriction and ligation techniques.

Alternatively, amplification may be accomplished by using a first probe which is complementary to a portion of the vector at or near the 3' terminus of the vector insert and a second probe which is complementary to a portion of the vector at or near the 5' terminus of the vector insert. Amplification using such probes allows for complete amplification of the entire vector insert for each member of the population. Upon size selection, larger inserts or full-length segments of the desired nucleic acid molecule may be obtained for further processing. Typically, such amplification may require amplification of long templates. Amplification of long templates (5 to 12 Kb; Long PCR) may be accomplished by using a combination of a DNA polymerase lacking 3' exonuclease activity and a DNA polymerase having 3' exonuclease activity (see U.S. Pat. No. 5,435,149). Such combination of polymerases are available commercially such as Elongase™ from Life Technologies, Inc. (Gaithersburg, Md.).

Figure 3:
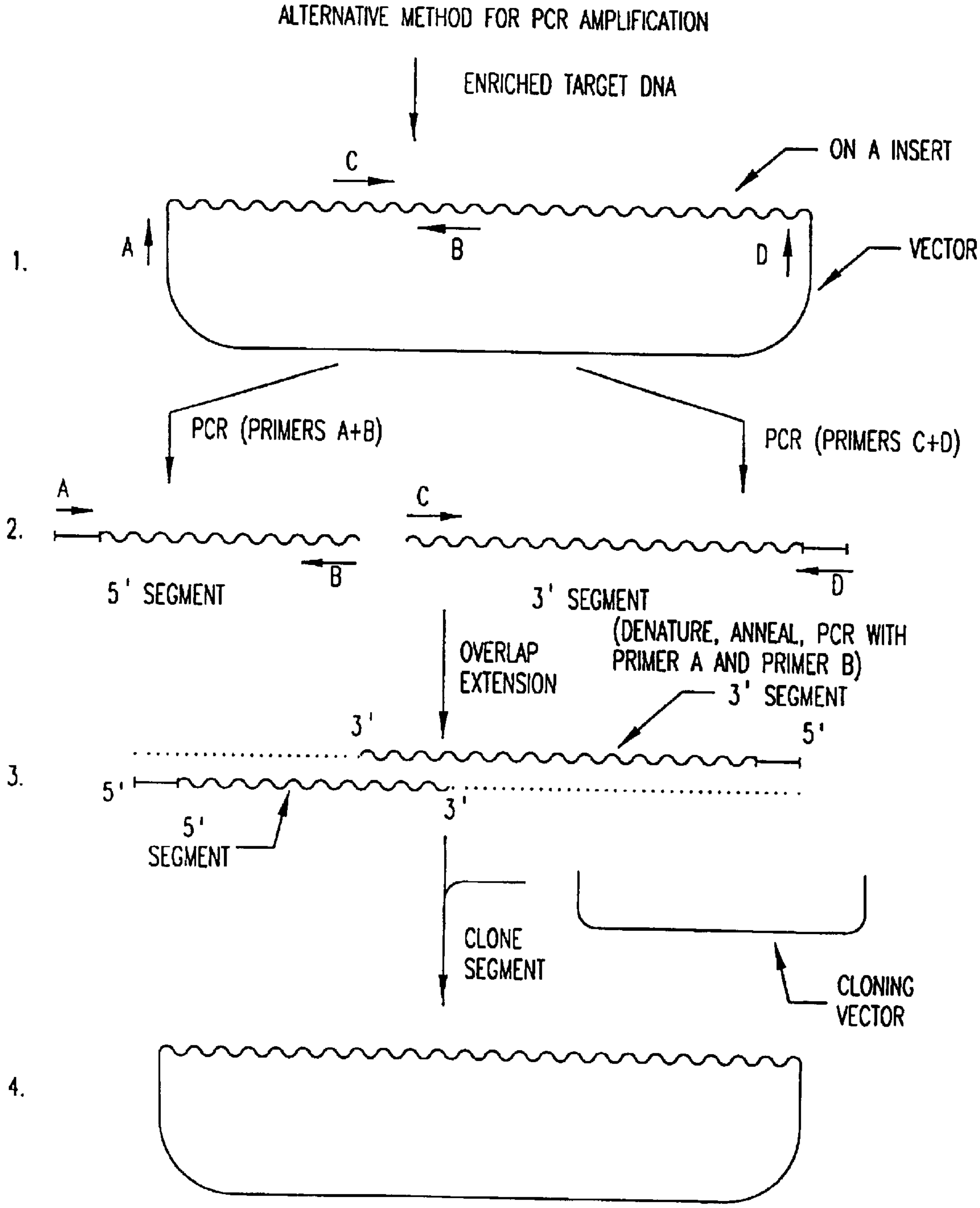
FIG. 3 provides a diagrammatic view of a preferred method for performing PCR on an enriched population of molecules.

In another aspect of the invention, larger or full-length nucleic acid molecules may be selected by using a combination of amplification probes. In this embodiment, a first probe complementary to a portion of the vector sequence at or near the 3' terminus of the insert, a second probe complementary to a portion of the vector sequence at or near the 5' terminus of the insert, a third primer complementary to a first portion of the vector insert, and a fourth primer complementary to a second portion of the vector insert may be used (see FIG. 3). Upon amplification using such primers, a first amplified region containing a 5' terminus of the vector insert and a second amplified region containing the 3' terminus of the insert is amplified. After amplification, both segments may be linked by an overlapped extension reaction (Horton et al., *Gene* 77:61–68(1989); Jayaraman et al., *Proc. Natl. Acad. Sci.* (*U.S.A.*) 88:4084–4088(1991)) in which the overlap of the two segments is used to join the two segments into a single segment. In this manner, the entire insert of the vector may be amplified without the need for long template amplification (above) or this amplification process may allow for amplification of extremely long inserts by combining long amplification with overlap extension reactions. After amplification, the larger or full-length inserts can be selected by size from the population.

This aspect of the invention is of particular interest for enriching for full-length genes obtained from a cDNA library. When preparing cDNA from the mRNA template, the first strand reaction typically provides a population of cDNA molecules (a portion of which are full-length) due to the failure of reverse transcriptase to completely synthesis cDNA from the mRNA template. The cDNA library comprises a population of cDNA molecules encoding significant numbers of genes (encoded by the tissue or cell from which the RNA was isolated) and as noted for each gene there is a subpopulation of cDNA molecules of varying sizes (some of which are full-length). The invention specifically provides a means to select a gene specific subpopulation (which then can be used for enrichment of full-length molecules) from the cDNA library. This aspect of the invention specifically comprises:

(a) contacting a single-stranded cDNA library with one or more haptenylated nucleic acid probes comprising a nucleotide sequence complementary to a nucleotide sequence of one or more desired target molecules (e.g. gene specific probes);

(b) isolating said desired target molecules with one or more binding ligands conjugated to a support; and (c) amplifying all or a portion of said desired target molecules and separating said amplified molecules according to size.

C. Polymerase Enrichment/Selection of Desired Molecules

In another preferred embodiment, a polymerase enrichment/selection protocol can optionally be used to aid, or further aid, in effecting the isolation of a desired target molecules. In this embodiment, a nucleic acid primer molecule having a nucleotide sequence complementary to a region of the desired target nucleic acid molecule is introduced into the reaction. A polymerase and appropriate nucleotides are also added, and the reaction is incubated under conditions sufficient to permit the primer to hybridize to the above-described single-stranded molecule (which is preferably a single stranded circular molecule), and to mediate the extension of the primer to form a double-stranded desired target nucleic acid molecule.

In one sub-embodiment, the primer molecule may have a nucleotide sequence that is complementary to the same region (or a subset or extension of the same region) as that which had been hybridized to the above-described probe. In such a case, the primer molecule maintains a selection for molecules of the initial sample that contains a single particular region (e.g., a promoter, enhancer, gene of interest, etc.). Preferably, stringent hybridization conditions are used and the conversion of single stranded nucleic acid to double stranded nucleic acid is done at high temperature with a thermostable polymerase, e.g., Taq polymerase. In this case, because the hybridization and double-strand conversion are done under conditions favorable to correct hybrids, the conversion step further enriches for or selects for the desired target molecules.

In an alternative sub-embodiment, the nucleotide sequence of the primer molecule is selected to be different from that of the probe, such that the primer molecule will hybridize to a region of the desired molecule other than the region that had been previously hybridized to the probe. This sub-embodiment permits one to select a subset of desired molecules that possess a further desired characteristic. For example, if the probe molecule hybridized to a particular enhancer element, the capture selection step described above would enrich for those members of the original mixture or library that contained the enhancer element. By employing a primer complementary to a particular receptor binding site, promoter element, gene sequence, terminator, etc., one would obtain double-stranded molecules that comprise that subset of the original mixture or library that contained both the enhancer element and the particular receptor binding site, promoter element, gene sequence, terminator, etc.

As indicated above, double-stranded nucleic acid molecules (e.g., DNA) transforms more efficiently than single-stranded nucleic acid molecules, hence, by transforming bacteria or eukaryotic cells with the double-stranded molecules obtained from the first or second sub-embodiments, and then recovering nucleic acid molecules from the transformants, one is able to obtain a substantial enrichment for the desired target nucleic acid molecules.

In some cases, such as where the prevalence of desired target molecules is low, it may be desirable to eliminate undesired single-stranded non-target molecules that remain after the double-strand conversion of target molecules. This may be accomplished by conducting the template-dependent extension of the primer in the presence of at least one "nucleotide analog" (either in lieu of or in addition to the naturally occurring non-analog). A "nucleotide analog", as used herein, refers to a nucleotide which is not found in the target DNA or RNA that is the primer's template. For example, where the isolated target molecule is DNA, suitable nucleotide analogs include ribonucleotides, 5-methyl-deoxcytosine, bromodeoxyuridine, 3-methyldeoxy-adenosine, 7-methyl-guanine, deoxyuridine, and 5,6-dihyro-5,6-dihydroxydeoxythymidine, etc. (see, Duncan, B. K., The Enzymes XIV:565–586 (1981)). Other nucleotide analogs will be evident to those of skill in the art. Where the template is RNA, deoxynucleotide triphosphates and their analogs are the preferred nucleotide analogs.

The presence of the nucleotide analog in the reaction will result in the production of a double-stranded molecule that contains incorporated analog bases. Such incorporation affects the ability of endonucleases and exonucleases to cleave or degrade the double-stranded molecule. Thus, if a primer is extended from a circular DNA template in the presence of a methylated nucleotide (for example, 5-methyl dCTP), the resulting double-stranded molecule, which contains incorporated 5-methyl C residues, is resistant to cleavage by many restriction endonucleases. HhaI is particularly preferred when used in conjunction with 5-methyl C residues, since it also degrades single-stranded DNA, the effect of incubation in the presence of such enzymes is to destroy most or all residual undesired non-target molecules present, and to thereby greatly enrich the concentration of the desired vector. Other nucleotide analogs that inhibit or block exonucleases or restriction endonucleases are 6-methyladenine, 5-methyl-guanine and 5-methylcytidine. Combinations of nucleotide analogs and suitable enzymes may be used in the invention and are known in the art (see, for example, Life Technologies™ 1993–1994 Catalogue and Reference Guide, Chapter 6, Life Technologies, Inc. (Gaithersburg, Md.), herein incorporated by reference).

In a similar manner, where the source library was composed of single-stranded RNA vectors, the use of dNTPs (i.e. dATP, dTTP, dCTP, and dGTP) in the conversion step will render such molecules resistant to mung bean nuclease, or Bal-31 nuclease.

Although the foregoing discussion has emphasized the use of circular molecules, the methods of the present invention are fully amenable to the use of linear molecules. In such a case, the primer molecule (but not necessarily the probe molecule) is preferably selected such that it hybridizes to the 5' terminus of the target molecule. Such selection will permit the template-dependent extension of the molecule to produce a full length copy of the target molecule.

Desirably, the recovered target molecules are then precipitated with organic solvents, and resuspended in buffer. The product may then be transformed or electroporated into recipient cells, for example by the method of Rubenstein et al. (*Nucl. Acids Res.* 18: 4833 (1990), herein incorporated by reference). Any recipient cell may be used, including prokaryotic or eukaryotic cells, although prokaryotic cells and bacteria, such as gram negative bacteria, are preferred. Particularly preferred gram negative bacteria include *E. coli, Salmonella, Klebsellia,* etc. Electrocompetent and chemically competent *E. coli* may be obtained from Life Technologies, Inc. (Gaithersburg, Md.).

Having now generally described the invention, the same will be more readily understood through reference to the following examples which are provided by way of illustration, and are not intended to be limiting of the present invention, unless specified.

EXAMPLE 1

Method for Isolating Desired Target Molecules

Preparation of Single-Stranded DNA

A preferred method for isolating a desired target molecule employs a library (preferably a cDNA library) in a single-stranded phagemid, such as M13 or preferably, vectors such as pSPORT 1, pCMV•SPORT, pZL1 (λZiplox®), and Blue-Script SK (+). In a typical reaction, 5 μg of double-stranded phagemid and 2 μl of 10× Gene II buffer (200 mM Tris (pH 8.0), 800 mM NaCl, 25 mM $MgCl_2$, 20 mM β-mercaptoethanol, 50% glycerol, 50 mg/ml BSA) was incubated with 1 μl of Gene II (10 units/μl), in a reaction volume of 20 μl. The reaction mixture was vortexed and then centrifuged at room temperature for 2 seconds at 14,000×g prior to being incubated at 30° C. for 30 minutes. The reaction was terminated by heating the mixture at 65° C. for 5 minutes and then immediately thereafter chilling the mixture on ice for 1 minute. After the reaction was terminated, 1 μl of the mixture was transferred to a new microcentifuge tube containing 9 μl TE buffer (10 mM Tris-HCl (pH 8.0), 1 mM EDTA) and 2 μl of 6× gel loading buffer (0.25% bromophenol blue, 0.25% xylene cyanol, 15% ficoll (type 400 in water)) and retained at 4° C. for later agarose gel analysis.

To the remaining 19 μl of reaction mixture, 2 μl of Exonuclease III (65 units/μl) was added. Before incubation, the reaction mixture was vortexed and centrifuged at room temperature for 2 seconds at 14,000×g. The reaction mixture was then incubated at 37° C. for 1 hour and then stored on ice. 1 μl of the reaction mixture was transferred to new microcentifuge tube containing 9 μl TE buffer (10 mM Tris-HCl (pH 8.0), 1 mM EDTA) and 2 μl of gel loading dye and retained at 4° C. for later agarose gel analysis.

The samples retained for agarose gel analysis were loaded on a 0.8% agarose gel in 1×TAE buffer (40 mM Tris-acetate (pH 8.3), 1 mM EDTA) to determine whether the double stranded DNA was converted to single stranded DNA by the Gene II/Exonuclease III digestion. Typically, more than 50% of the supercoiled DNA should be nicked by the Gene II protein and migrate as relaxed circular DNA and the nicked form of the double-stranded DNA generated by Gene II treatment should be completely converted to single-stranded DNA after Exonuclease III digestion. If the double stranded DNA (ds-DNA) is converted to single stranded (ss-DNA), then hybridization with the probe is performed (see below).

Preparation of Biotinylated Oligonucleotides

The oligonucleotide probes were biotin-labeled using biotin-14-dCTP and terminal deoxynucleotidyl transferase (TdT) as described by Flickinger, J. L. et al. (*Nucleic Acids Res.* 20: 2382 (1992)) with some modifications. In a typical reaction, ≈3 μg of oligonucleotides (16–25-mer), 5 μl of 5×TdT buffer, 5 μl of biotin-14-dCTP (5 mM) and 2 μl of TdT in a reaction volume of 25 μl was incubated at 30° C. for 1 hour. The reaction was terminated by precipitating the probes with 1 μl of glycogen (20 μg/μl), 26 μl 1M Tris-HCl (pH 7.5) and 120 μl of ethanol and storing on dry ice for 10 minutes. After centrifugation at 4° C. for 30 minutes at 14,000×g, the probes were rinsed with 200 μl of 70% ethanol (−20° C.) and centrifuged for 2 minutes at 14,000×g at room temperature. The probes were air-dried and dissolved in 20 μl of TE. To determine the labeling efficiency and the concentration of the labeled probe, 4 μl of labeled products were resuspended in an equal volume of 90% formamide, 50 mM Tris-base, 45 mM boric acid, 0.5 mM EDTA, 0.1% bromophenol blue and 0.1% xylene cyanol. The probes were electrophoresed along with a known amount of the starting material on 16% denaturing PAGE. The gel was stained in an ethidium bromide solution (0.5 μg/ml) for 15 minutes, and photographed.

Hybrid Selection

The hybridization was performed by the following procedure: to the remaining 20 μl of Gene II/Exonuclease III treated DNA was added and mixed 7.0 μl of 4× Hybridization Buffer (100 mM HEPES (pH 7.5), 2 mM EDTA, 0.2% SDS). The mixture was mixed by repeat pipeting. The DNA was denatured at 90° C. for 1 minute and immediately chilled in ice water for 1 minute. 1 μl (20 ng) of biotin-probe was added to the DNA mixture and the mixture was incubated at 37° C. for 1 hour.

Before binding the hybrids to the streptavidin beads, 45 μl of the streptavidin coated paramagnetic beads (Life Technologies, Inc., Gaithersburg, Md.) were washed once with 100 μl TE. The paramagnetic beads were resuspended in 30 μl of TE.

After incubating the reaction mixture for 1 hour, the reaction mixture was centrifuged for 2 seconds at 14,000×g. 30 μl of resuspended beads was added to the hybridization mixture (27 ml) and mixed well by gentle pipeting. The mixture was incubated at room temperature for 30 minutes with occasional mixing by gently tapping the tube. The paramagnetic beads were separated from the DNA by inserting the tube into the magnet and washed 4 times with 100 μl of wash buffer (10 mM Tris (pH 7.5), 1 mM EDTA).

Finally, the paramagnetic beads were resuspended in 10 μl of 1× elution buffer (10 mM glycine) and incubated at room temperature for five minutes while being gently agitated. The supernatant was then removed and retained in a new tube while the beads were resuspended in 7 μl of elution buffer. The tube containing the resuspended beads was inserted into the magnet for five minutes and the aqueous phases were pooled (26 μl total). The tube containing the pooled supernatants was inserted into the magnet for 10 minutes to eliminate any remaining beads.

Repair of Single-Stranded DNA

A DNA repair mix containing 1 μl (50 ng) of unlabeled primer, 17 μl of the eluted single-stranded DNA, 0.5 μl dNTP mix (10 mM), 0.5 μl repair enzyme (Dynazyme, 2 units/μl), 2.0 μl of 10× repair buffer (100 mM Tris (pH 8.8 at 25° C.), 15 mM $MgCl_2$, 500 mM KCl, 1% Triton X-100) was incubated at 90° C. for 1 minute, 55° C. for 30 seconds and then 70° C. for an additional 15 minutes. Following these incubations, the reaction mixture was centrifuged for 2 seconds at 14,000×g. After repair, the double-stranded DNA was stored at −20° C.

Detection of the Target Gene

The repaired DNA is used to transform *E. coli* bacteria by chemical transformation or electroporation using techniques well known to those of ordinary skill in the art. For transformation, cells obtained from Life Technologies, Inc. are used according to the following procedure: UltraMax competent cells are removed from −70° C. and thawed on wet ice. Immediately after thawing, the cells are gently mixed and 100 μl of competent cells are aliquoted into chilled polypropylene tubes. To determine transformation efficiency, 5 μl (0.05 ng) control DNA to one tube containing 100 μl competent cells. For each captured or repaired DNA reaction, mix 3 μl of the repaired DNA into an individual tube of cells (store the remainder of the DNA reaction at −20° C.) and incubate on ice for 30 minutes. The cells are then heat shocked for 45 seconds in a 42° C. water bath without shaking and then stored on ice for 2 minutes. Following these incubations, 0.9 ml of S.O.C. medium is added and the cells are shaked at 225 rpm for 1 hour at 37° C. For the control plasmid, the cells are diluted (1:400) and 100 μl of the diluted cells are then spread on LB or YT plates containing 100 μg/ml ampicillin. For the captured or repaired cDNA samples, plate 100 μl and 200 μl aliquots onto LB plates containing 100 μg/ml ampicillin (e.g. pSPORT vector). The remainder of the cells are centrifuged for 15 seconds in an autoclaved 1.5 ml microfuge tube, the supernatant is discarded, the cells are resuspended in 200 μl of S.O.C. medium and plated onto an ampicillin plate. The plates are incubated overnight in a 37° C. incubator. For electroporation, electrocompetent cells (e.g. DH10B) were obtained from Life Technologies, Inc. and transformed according the procedure provided by the manufacturer (see GeneTrapper Manual). After transformation or electroporation, the target colony can be detected by the PCR, colony hybridization or cycle sequencing approach.

Preferably the target gene is identified using PCR essentially as follows. The repaired DNA is used to transform *E. coli* bacteria. The resulting library is referred to as an enriched library. Each individual colony is added to an eppendorf tube containing 20 μl of 1× PCR buffer (50 mM KCl, 20 mM Tris-HCl (pH 8.4)), 0.2 mM dNTP mix, 0.2 μM primers, 1.5 mM $MgCl_2$ and 0.5 units Taq DNA polymerase. The tubes are placed in a thermal cycler prewarmed to 94° C. PCR is performed using the following program: 1 cycle: 94° C./2 minutes; 30 cycles of 94° C./30 seconds, 55° C./30 seconds, 72° C./2 minutes. After PCR, the presence of specific amplified products is evaluated by gel electrophoresis of an aliquot of the reaction mixture. The presence of a PCR product of the correct size confirms the presence of a desired clone.

EXAMPLE 2

Alternative Method for Isolating Desired Target Molecules

An alternative method for isolating a desired target molecule employs a library or mixture of a single-stranded phagemid, such as M13. In such a method, the single-stranded phagemid is introduced into an ung dut mutant of *E. coli* (Kunkel, T. A., U.S. Pat. No. 4,873,192; Longo, M. C. et al., *Gene* 93:125–128 (1990); Hartley, U.S. Pat. No. 5,035,966; all herein incorporated by reference). The "+" strand of phagemids grown in such mutants contains deoxyuridine (dUTP), and can be recovered from the packaged virion. Thus, the use of such mutants permits the isolation of a library or mixture that comprises single-stranded DNA molecules which contain dU residues (Kunkel, T. A., U.S. Pat. No. 4,873,192).

The recovered DNA can then be optionally isolated via a capture step, or directly processed using a nuclease enrichment step.

If a capture step is to be conducted, the dU-containing strands are incubated in the presence of a complementary biotinylated probe. The probe, and any hybridized DNA is then recovered by permitting the biotin to bind to avidin or strepavidin coated paramagnetic beads, and then recovering the beads from solution using a magnet. The library or mixture is recovered from the beads by denaturation of the hybridized molecules.

The recovered single-stranded DNA is then incubated in the presence of a complementary primer, dATP, dTTP, dCTP, and dGTP and under conditions sufficient to permit the extension of the primer. Such extension thus creates a sample that contains single-stranded dU-containing molecules and double-stranded dU/dT hybrid (desired target) molecules.

Although the triphosphate form of deoxyuridine, dUTP, is present in living organisms as a metabolic intermediate, it is rarely incorporated into DNA. When dUTP is incorporated into DNA, the resulting deoxyuridine can be promptly removed in vivo by the enzyme uracil DNA glycosylase (UDG) (Kunkel, U.S. Pat. No. 4,873,192; and Duncan, B. K. The Enzymes XIV:565–586 (1981), both references herein incorporated by reference in their entirety).

In this embodiment of the present invention, the mixture of molecules is then treated, either in vivo or in vitro with UDG. Such treatment destroys all of the single-stranded, non-desired, non-target molecules in the sample. It further destroys the "+" strand of all of the double-stranded desired target molecules.

The sample is therefore then either directly transformed into *E. coli* to permit the isolation of the target molecule or incubated in the presence of a primer molecule that is capable of hybridizing to the "−" strand of the phagemid. Such incubation is under conditions suitable for mediating the template-dependent extension of the primer. Hence, such incubation produces double-stranded molecules that have the sequence of the desired target molecules, and thereby permit the isolation of the target molecule.

EXAMPLE 3

Alternative Method for Preparation of Single-Stranded DNA

The large scale preparation of single-stranded phagemid cDNA library may be made as described previously (Gruber, C. E. et al., *Focus* 15: 59–65 (1993), herein incorporated by reference).

EXAMPLE 4

Alternative Method for Preparation of Biotinylated Oligonucleotides

The oligonucleotide probes were biotin-labeled using biotin-14-dCTP and terminal deoxynucleotidyl transferase (TdT) as described by Flickinger, J. L. et al. (*Nucleic Acids Res.* 20: 2382 (1992)) with the following minor modifications. In a typical reaction, 0.3–0.5 nmol (≈5 μg) of oligonucleotides (21–25-mer), 500 μM of biotin-14-dCTP and 60 units of TdT in 50 μl of 1× tailing buffer (100 mM potassium cacodylate (pH 7.2), 2 mM $CoCl_2$ and 200 μM DTT) are incubated at 37° C. for 15 minutes. The reaction is terminated by adding 2 μl of 0.25 M EDTA. The labeled probes are precipitated by adding an equal volume (52 μl) of 1 M Tris buffer (pH 7.5), 10 μg glycogen as carrier, and 2.5 volumes (260 μl) of ethanol, and stored on dry ice for 10 minutes. After centrifugation at 4° C. for 10 minutes, the probes are rinsed with 100 μl of 75% ethanol and centrifuged for 2 minutes. The probes are air dried and dissolved in 10 μl of TE. To determine the labeling efficiency and the concentration of the labeled probe, 2 μl of labeled products are resuspended in an equal volume of sequencing reaction stop buffer (95% (v/v) formamide, 10 mM EDTA (pH 8.0), 0.1% (w/v) bromophenol blue, 0.1% (w/v) xylene cyanol), heated at 95° C. for 1 minute and chilled on ice. The probes are electrophoresed along with a known amount of the starting material on 16% denaturing PAGE. The gel is stained in an ethidium bromide-solution (0.5 μg/ml) for 15 minutes, and photographed. Typically, more than 95% of the oligonucleotide will be labeled. The concentration of the labeled probes is determined by the comparison to the known staring material.

EXAMPLE 5

Alternative Method for Hybrid Selection

The hybridization is performed by the following procedure: 1–10 μg of single-stranded target library DNA is diluted with 10 μl of dilution buffer (100 mM HEPES (pH 7.5), 2 mM EDTA and 0.2% SDS) to a final volume of 19 μl in a 5 ml Falcon tube. The DNA is denatured at 95° C. for 1 minute and immediately chilled in ice water for 5 minutes. 1 μl (20 ng) of biotin-probe is added to the DNA mixture, followed by the addition of 5 μl of 5 M NaCl. The hybridization mixture is incubated at 42° C. with continuous shaking (200 rpm) in a culture incubator for 24 hours. Before binding the hybrids to the streptavidin, 50 μl of the streptavidin coated paramagnetic beads (DYNAL) are washed once with 1× binding buffer (10 mM TRIS (pH 7.5), 1 mM EDTA and 1 M NaCl) by following the manufacturer's instructions. The paramagnetic beads are resuspended in 20 μl of 1× binding buffer. The hybridization mixture is added to the resuspended beads and mixed well. The mixture is incubated at room temperature for 1 hour with occasional mixing by gently tipping the tube. The paramagnetic beads are separated from the DNA bulk by inserting the tube into the magnet, and washed 6 times with the washing buffer (10 mM Tris (pH 7.5), 1 mM EDTA and 500 mM NaCl). Finally, the paramagnetic beads are resuspended in 20 μl of 30% formamide in TE buffer. The selected DNA is released by heating the beads at 65° C. for 5 minutes. The tube is inserted into the magnet, and the aqueous phase is transferred to a new tube. The beads are washed once with 15 μl of TE buffer, and the aqueous phases are pooled. The selected DNA is precipitated with 0.5 volumes of 7.5 M ammonium acetate, 10 μg of glycogen, and 2.5 volumes of ethanol. The DNA pellet is dissolved in 5–10 μl of TE buffer. An aliquot (1 μl) is used for electroporation to determine the hybrid selection efficiency.

EXAMPLE 6

Alternative Method for Repair of Single-Stranded DNA

The remainder of the selected single-stranded DNA is converted to double-stranded DNA before electroporation as described by Rubenstein et al. (*Nucl. Acids Res.* 18: 4833 (1990)) with some modifications. The reaction is carried out in 30 μl containing the selected single-stranded DNA, 250 ng of unlabeled primer, 300 μM each dTTP, dGTP, dATP and 5-methyl dCTP, Taq DNA polymerase buffer and 2 units of Taq DNA polymerase. After repair, the mixture is extracted once with phenol:chloroform. The organic phase is back-extracted with 15 μl of TE, the aqueous phases are pooled and ethanol precipitated. The pellet is rinsed with 100 μl of 75% ethanol and dried. The repaired DNA is dissolved in 5–10 μl of TE and digested with HhaI for 2 hours at 37° C. After digestion, the mixture is extracted once with phenol:chloroform, ethanol precipitated and dissolved in 5–10 μl of TE.

EXAMPLE 7

Methods for Enrichment of Full Length cDNA Molecules using PCR Amplification

In another embodiment of the present invention, the present invention may be used to preferentially isolate cDNA molecules containing larger DNA inserts. A cDNA library is generated according to the procedure set forth in Example 3. To select for target molecules from the cDNA library, the selection method of Example 1 is used. The isolated target molecules are then subjected to size enrichment.

For this purpose, two PCR reactions are set up and carried out essentially as set forth in Example 1. Each PCR reaction uses a pair of PCR primers, one complementary to the target sequence and one complementary to the vector sequence (see FIG. 3, steps 1 and 2). The PCR products are then used in an overlap extension reaction (Horton et al., *Gene* 77:61–68 (1989); Jayaraman et al., *Proc. Natl. Acad. Sci.* (*USA*) 88:4084–4088 (1991)) (see FIG. 3, step 3). The products of primer extension reaction are then separated by gel electrophoresis and may be then cloned into an appropriate vector, e.g. a TA vector, prior to transformation of an appropriate host cell. Colonies after transformation are tested for the presence of the target sequence by colony PCR and selected colonies may be tested by DNA sequencing.

EXAMPLE 8

Comparison of Elution Buffers

A novel elution buffer was developed to remove the biotinylated capture probe hybridized to the target nucleic acid molecule (e.g., cDNA molecule). Originally a 30% formamide/TE (pH 8.0) buffer was used which required an ethanol precipitation following its use. A novel elution buffer containing 10 mM glycine was shown to be effective and when compared with the formamide/TE buffer produced more colonies and a higher percentage of these were positive for the CAT plasmid target that was mixed in the cDNA library at a ratio of 1:50,000.

TABLE 1

| Elution Buffer | # of ampicillin resistant colonies | # of chloroamphenicol resistant colonies | % CAT |
|---|---|---|---|
| 30% formamide/ TE pH 8.0 | 75 | 41 | 55 |
| 10 mM glycine | 250 | 162 | 65 |

In addition to 10 mM glycine, 15 other amino acids/amino acid analogs were tested and shown to be effective as an elution buffer, including the following amino acids: alanine, arginine, aspargine, glutamine, isoleucine, leucine, methionine, phenylalanine, proline, serine, threonine, tryptophan, tyrosine, valine, and the nitrogenous base, imidazole (see Example 11).

EXAMPLE 9

Use of dP and dK Containing Degenerate Oligonucleotides

A comparison was made using the procedure of Example 1 using degenerate biotinylated probes containing dP and dK. These probes had a degeneracy of 1,024 with the same oligonucleotide in which dK had been substituted for the A/G degenerate position, dP for the C/T degenerate position and dP/dK for all four nucleotides. In effect, each substitution with dP or dK reduces the complexity of the oligonucleotide population by a factor of 2.

When a pSPORT1 plasmid containing the chloramphenicol (CAT) gene is mixed at 1:50,000 with a cDNA library, the percent positive (ie., CAT clones) increases 4-fold favoring the dP-dK substituted oligonucleotide as depicted in Table 2.

TABLE 2

| | # of ampicillin resistant colonies | # of chloroamphenicol resistant colonies | % CAT |
|---|---|---|---|
| D1024-expt1 | 308 | 31 | 10 |
| D1024-expt2 | 346 | 34 | 9.8 |
| D1024-PK-expt1 | 126 | 50 | 39.7 |
| D1024-PK-expt2 | 151 | 65 | 43 |

Oligonucleotide D1024 (GTN TG(T/C) GA(T/C) GGN TT(T/C) CA(T/C) GTN GG) (Seq ID NO 1) has a degeneracy of 1024. The sequence in which dK is substituted for the A/G degenerate position, dP for the C/T degenerate position and dP/dK for all four nucleotides is given by GT(dP/dK) TG(dP) GA(dP) GG(dP/dK) TT(dP) CA(dP) GT(dP/dK) GG (Seq ID NO 12). The sequences represented by oligonucleotide D1024-PK, which has a degeneracy of 8, are depicted in Table 3.

TABLE 3

| SEQ ID NO | Sequence |
|---|---|
| 2 | GTK TGP GAP GGK TTP CAP GTK GG |
| 3 | GTK TGP GAP GGK TTP CAP GTP GG |
| 4 | GTK TGP GAP GGP TTP CAP GTK GG |
| 5 | GTP TGP GAP GGK TTP CAP GTK GG |
| 6 | GTP TGP GAP GGK TTP CAP GTP GG |

TABLE 3-continued

| SEQ ID NO | Sequence |
|---|---|
| 7 | GTK TGP GAP GGP TTP CAP GTP GG |
| 8 | GTP TGP GAP GGP TTP CAP GTK GG |
| 9 | GTP TGP GAP GGP TTP CAP GTP GG |

EXAMPLE 10

Use of 5-methyl Deoxycytosine (5mC)/HhaI in the Repair Reaction

Experiments have reproducibly shown that the inclusion of the methylated nucleotide 5mC in combination with the enzyme HhaI can reduce the number of background colonies. Using a mixture of the CAT plasmid described in Example 9 above with a cDNA library at 1:50,000, experiments as essentially described in Example 1 (with or without 5 mC) were used to compare the effect of the repair reaction using nuclease resistant analogs. The data presented in Table 3 demonstrates that the background can be reduced when the 5 mC protocol, described below, is used.

The DNA primer/repair mixture for each capture reaction was prepared, on ice, by adding to the captured DNA (26 μl) tube 1 μl of unbiotinylated oligonucleotide (50 ng), 0.5 μl of dATP, dGTP, dTTP and 5-methyl d-CTP mix (10 mM each), 3 μl of 10× Repair Buffer, 0.5 μl (1 unit) Repair Enzyme. The DNA primer/repair mixture was mixed by repeat pipetting and centrifuged at room temperature for 2 seconds at 14,000×g. After centrifugation, the DNA primer/repair mixture was incubated at 85° C. for 1 minute, incubated at 55° C. for 30 seconds, and incubated at 70° C. for 15 minutes to allow for primer extension. After incubating for 15 minutes at 70° C., the tubes were centrifuged for 2 seconds and cooled to room temperature. After the tubes had cooled to room temperature, 1 μl of HhaI (0.25–0.5 units) was added to the reaction mixture, mixed, centrifuged for 2 is seconds at 14,000×g, and incubated at 37° C. for 30 minutes. After the 30 minute incubation, the DNA was transferred to a fresh tube and precipitated by adding 1 μl of glycogen (20 μg), 4 μl of 3M sodium acetate, and 90 μl of ethanol. The tubes were incubated on ice for at least 10 minutes and then centrifuged for 30 minutes at 4° C. The supernatant was decanted and the DNA pellet was washed with 100 μl of 70% ethanol (−20° C.) and centrifuged at room temperature for 2 minutes. The ethanol was decanted, the DNA pellet was dried at room temperature for 5–10 minutes, and the DNA pellet was resuspended in 10 μl of TE. DH10B competent cells were electroporated with 2 μl of each sample.

TABLE 3

| | # of ampicillin resistant colonies | # of chloroamphenicol resistant colonies | % CAT |
|---|---|---|---|
| no 5mC-expt1 | 210 | 138 | 65.2 |
| 5mC-expt2 | 124 | 76 | 61.5 |
| no 5mC-expt1 | 63 | 58 | 92 |
| 5mC-expt2 | 71 | 67 | 95 |

EXAMPLE 11

Assay For Determining Denaturation Of Double-Stranded Nucleic Acid Molecules With Amino Acid Denaturants A protocol was developed to determine the ability of amino acid denaturants to denature or separate double-stranded nucleic acid molecules to form single-stranded nucleic acid molecules (e.g., double-stranded DNA to form single-stranded DNA molecules). In this method, pSPORT I-CAT DNA is used as a template for partial repair with DNA polymerase and radio-labeled nucleotides. Specifically, 0.7 μg of single-stranded pSPORT I-CAT DNA was partially repaired with primer and P32-dCTP/dNTPs as described in Example 1 (repair of single-stranded DNA), except that the denaturation at 90° C. and the incubation at 70° C. was performed for 4 minutes rather than 15 minutes. After the partial repair reaction, 25 ng of P32-labeled pSPORT ICAT DNA in 17 μl of 1× GENE II buffer was hybridized to a biotinylated probe (SEQ ID NO 10) (GAC CGT TCA GCT GGA TAT TAC GGC C)) and the hybridized molecules were captured on strepavidan magnetic beads as described in Example 1 (hybrid selection). The beads were washed 4 times with wash buffer (10 mM Tris (pH 7.5), 1 mM EDTA) and the hybridized molecules were then tested with amino acid solutions to determine the effect of the amino acid solutions as denaturants.

In this assay, the ability of the amino acid denaturants to remove radioactivity from the solid support (e.g. the beads) indicated that the amino acid denaturants has the ability to denature or separate the double-stranded nucleic acid molecules. Tests were performed using 10 mM concentrations of amino acid in solution. A number of amino acid solutions (10 mM) acted as denaturants in this assay. These amino acid denaturants include glycine, alanine, asparagine, glutamine, isoleucine, leucine, methionine, phenylalanine, proline, serine, threonine, tryptophan, tyrosine, valine and imidazole. As will be appreciated, other amino acids, their derivatives or analogs as well as polyamino acids (their derivatives or analogs) may be used as denaturants in accordance with the invention. The concentrations of such amino acid denaturants which are optimal for denaturization may be determined using the above assay by one of ordinary skill in the art.

EXAMPLE 12

Use of Degenerate Kozak Consensus Sequence Oligonucleotides to Isolate cDNA Clones Containing the Translation Initiation Codon In another embodiment of the present invention, the present invention may be used to preferentially isolate cDNA molecules that contain the 5' terminus including the translation initiation codon. This is accomplished by developing degenerate oligonucleotide to the Kozak sequence which includes the translation initiation codon and extends 5' approximately 13 nucleotides (Kozak, M, *Nucleic Acids Res.* 8:125–32 (1987); Kozak, M, *J. Biol. Chem* 266:19867–70 (1991)). The consensus sequence for initiation of translation by eukaryotic ribosomes is GCC GCC (A/G)$^{-3}$CC A$^{1}$UG G$^{4}$ (SEQ ID NO 11), Kozak, M, *Nucleic Acids Res.* 8:125–32 (1987); Kozak, M, *J. Biol. Chem* 266:19867–70 (1991), herein incorporated by reference; Sambrook et al., 16.16, In *Molecular Cloning, a Laboratory Manual,* Cold Spring Harbor Press (1989), herein incorporated by reference. Two approaches can be attempted to enrich for the presence of the 5' terminus including the translation start codon. In the first, the degenerate Kozak oligonucleotide probe can be used to enrich by GeneTrapper for 5' sequences followed by the use of a gene-specific GeneTrapper probe. Alternatively, a gene-specific GeneTrapper probe can be applied to a phagemid cDNA library using GeneTrapper followed by the use of a degenerate Kozak oligonucleotide probe. In both cases, the percentage of clones that contain the 5' terminus including the translation initiation codon should be enriched. This method will be especially useful for clones derived from longer mRNAs (i.e., greater than 5 Kb).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

All patents, patent applications and publications referenced herein, are incorporated by reference in their entirety.

What is claimed is:

1. A method for hybridizing one or more nucleic acid molecules, said method comprising i) contacting one or more double-stranded nucleic acid molecules with a denaturant selected from the group consisting of a) one or more amino acid denaturants, b) imidazole, and c) one or more amino acid denaturants plus imidazole, thereby forming one or more single-stranded target nucleic acid molecules; and ii) combining said one or more single-stranded target nucleic acid molecules with one or more additional nucleic acid molecules wherein said one or more additional nucleic acid molecules are capable of hybridizing to said single-stranded target nucleic acid molecules thereby obtaining one or more of said hybridized nucleic acid molecules;

wherein said amino acid denaturants are selected from the ground consisting of one or more amino acids, polyamino acids, and combinations thereof; wherein said amino acid denaturants denature or separate double-stranded nucleic acid molecules.

2. The method of claim 1, wherein said polyamino acids comprise two or more amino acids.

3. The method of claim 1, wherein said amino acid denaturants are selected from the group consisting of glycine, D-alanine, L-alanine, DL-alanine, arginine, glutamine, isoleucine, leucine, methionine, phenylalanine, proline, serine, threonine, tryptophan, tyrosine, and valine.

4. The method of claim 1, wherein the concentration of said denaturants ranges from about 1 mM to about 500 mM.

5. The method of claim 4, wherein said concentration ranges from about 5 mM to about 50 mM.

6. The method of claim 5, wherein said concentration is about 10 mM.

7. The method of claim 1, wherein said amino acid denaturants are natural or unnatural amino acids.

8. The method of claim 1, wherein said one or more additional nucleic acid molecules is haptenylated.

9. The method of claim 1, wherein said one or more double-stranded nucleic acid molecules is a cDNA library.

10. The method of claim 1, wherein said one or more single-stranded target nucleic acid molecules is longer than said one or more additional nucleic acid molecules.

11. The method of claim 1, wherein said contacting and said combining occur in a homogenous solution.

12. The method of claim 1, wherein said contacting and said combining occur in a heterogenous reaction mixture.

13. A method for hybridizing one or more nucleic acid molecules, said method comprising i) contacting one or more haptenylated double-stranded nucleic acid molecules with a denaturant selected from the group consisting of
   a) one or more amino acid denaturants,
   b) imidazole, and
   c) one or more amino acid denaturants plus imidazole, thereby forming one or more non-haptenylated single-stranded nucleic acid molecules and one or more haptenylated single-stranded nucleic acid molecules; and ii) combining said one or more non-haptenylated single-stranded nucleic acid molecules with one or more additional nucleic acid molecules wherein said one or more additional nucleic acid molecules are capable of hybridizing to said non-haptenylated single-stranded nucleic acid molecules thereby obtaining one or more of said hybridized nucleic acid molecules;

wherein said amino acid denaturants are selected from the group consisting of one or more amino acids, polyamino acids, and combinations thereof; wherein said amino acid denaturants denature or separate double-stranded nucleic acid molecules.

14. The method of claim 13, wherein said one or more non-haptenylated single-stranded nucleic acid molecules are obtained from a cDNA library.

15. The method of claim 13, wherein said one or more haptenylated single-stranded nucleic acid molecules is shorter than said one or more non-haptenylated single-stranded nucleic acid molecules.

16. The method of claim 13, wherein said contacting and said combining occur in a homogenous solution.

17. The method of claim 13, wherein said contacting and said combining occur in a heterogenous reaction mixture.

18. The method of claim 13, wherein said amino acid denaturants are natural or unnatural amino acids.

19. The method of claim 13, wherein said polyamino acids comprise two or more amino acids.

20. The method of claim 13, wherein said amino acid denaturants are selected from the group consisting of glycine, D-alanine, L-alanine, DL-alanine, arginine, glutamine, isoleucine, leucine, methionine, phenylalanine, proline, serine, threonine, tryptophan, tyrosine, and valine.

21. The method of claim 13, wherein the concentration of said denaturants ranges from about 1 mM to about 500 mM.

22. The method of claim 21, wherein said concentration ranges from about 5 mM to about 50 mM.

23. The method of claim 22, wherein said concentration is about 10 mM.

* * * * *